United States Patent [19]
Mikhail et al.

[11] Patent Number: 5,624,395
[45] Date of Patent: Apr. 29, 1997

[54] URINARY CATHETER HAVING PALPITATABLE VALVE AND BALLOON AND METHOD FOR MAKING SAME

[75] Inventors: Adel A. Mikhail, Bloomington; Gene E. Stobbs; Adel M. Hashw, both of Brooklyn Park; Shelley N. Johnson, Minnetonka, all of Minn.

[73] Assignee: CV Dynamics, Inc., Inver Grove Heights, Minn.

[21] Appl. No.: 546,572

[22] Filed: Oct. 20, 1995

Related U.S. Application Data

[63] Continuation-in-part of Ser. No. 392,529, Feb. 23, 1995, abandoned.

[51] Int. Cl.$^6$ .................................................... A61M 11/00
[52] U.S. Cl. ........................... 604/93; 604/246; 604/250; 600/29; 128/DIG. 25
[58] Field of Search ............................ 604/96–104, 174, 604/256, 247, 349, 329, 54, 55, 93, 246, 250; 600/31, 29–30; 128/DIG. 25; 251/342; 137/849

[56] References Cited

U.S. PATENT DOCUMENTS

| | | |
|---|---|---|
| 274,447 | 3/1883 | Kennish . |
| 3,331,371 | 7/1967 | Rocchi et al. . |
| 3,438,375 | 4/1969 | Ericson . |
| 3,459,175 | 8/1969 | Miller . |
| 3,503,400 | 3/1970 | Osthagen et al. . |
| 3,731,670 | 5/1973 | Loe . |
| 3,758,073 | 9/1973 | Schulte . |
| 3,768,102 | 10/1973 | Kwan-Gett et al. . |
| 3,812,841 | 5/1974 | Isaacson . |
| 3,841,304 | 10/1974 | Jones . |
| 3,865,666 | 2/1975 | Shoney . |
| 3,924,634 | 12/1975 | Taylor et al. . |
| 3,959,429 | 5/1976 | Benning . |
| 3,967,645 | 7/1976 | Gregory . |
| 3,977,408 | 8/1976 | Mackew . |
| 3,985,601 | 10/1976 | Panagrossi . |
| 4,026,298 | 5/1977 | Grausz . |
| 4,188,542 | 2/1980 | Patel et al. . |
| 4,210,478 | 7/1980 | Shoney . |
| 4,222,384 | 9/1980 | Birtwell . |
| 4,225,371 | 9/1980 | Taylor et al. . |
| 4,284,459 | 8/1981 | Patel et al. . |
| 4,335,723 | 6/1982 | Patel . |
| 4,432,757 | 2/1984 | Davis, Jr. . |
| 4,457,299 | 7/1984 | Cornwell . |
| 4,553,959 | 11/1985 | Hirkey et al. . |
| 4,587,954 | 5/1986 | Haber . |
| 4,643,169 | 2/1987 | Koss et al. . |
| 4,710,169 | 12/1987 | Christopher . |
| 4,813,935 | 3/1989 | Haber et al. . |
| 4,822,333 | 4/1989 | Lavarenne . |
| 4,846,784 | 7/1989 | Haber . |
| 4,932,938 | 6/1990 | Goldberg et al. . |
| 4,946,449 | 8/1990 | Davis, Jr. . |
| 4,968,294 | 11/1990 | Salama . |
| 5,030,199 | 7/1991 | Barwick et al. . |
| 5,041,092 | 8/1991 | Barwick . |
| 5,078,676 | 1/1992 | Bailly . |
| 5,090,424 | 2/1992 | Simon et al. . |
| 5,114,398 | 5/1992 | Trick et al. . |
| 5,131,906 | 7/1992 | Chen . |
| 5,234,409 | 8/1993 | Goldberg et al. . |
| 5,306,226 | 4/1994 | Salama . |
| 5,360,402 | 11/1994 | Conway et al. . |

Primary Examiner—Vincent Millin
Assistant Examiner—Perry E. Van Over
Attorney, Agent, or Firm—Patterson & Keough, P.A.

[57] ABSTRACT

An indwelling urinary catheter having a palpitatable multi-axial dome-type valve and an inflatable anchoring balloon. The valve has a peripheral trough to maximize drainage. The catheter body and balloon are integrally molded from silicone to produce a uniform and symmetrical balloon shape. The balloon shape may be selectively altered by varying bonding patterns or wall thicknesses. Valve openings traverse an arcuate pathway, and adjacent valve elements are separated by an intermediate rib to ensure a reliable closure. Valve elements are readily displaced by a drainage tube connector that engages the valve body. A collar on the catheter body moves axially along helical threads to adjust tension on the balloon.

15 Claims, 14 Drawing Sheets

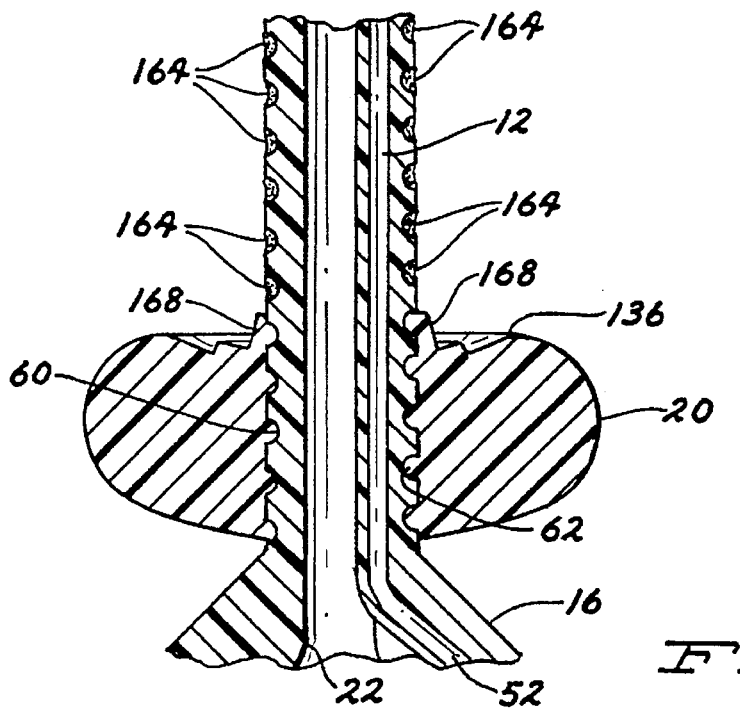
FIG. 43
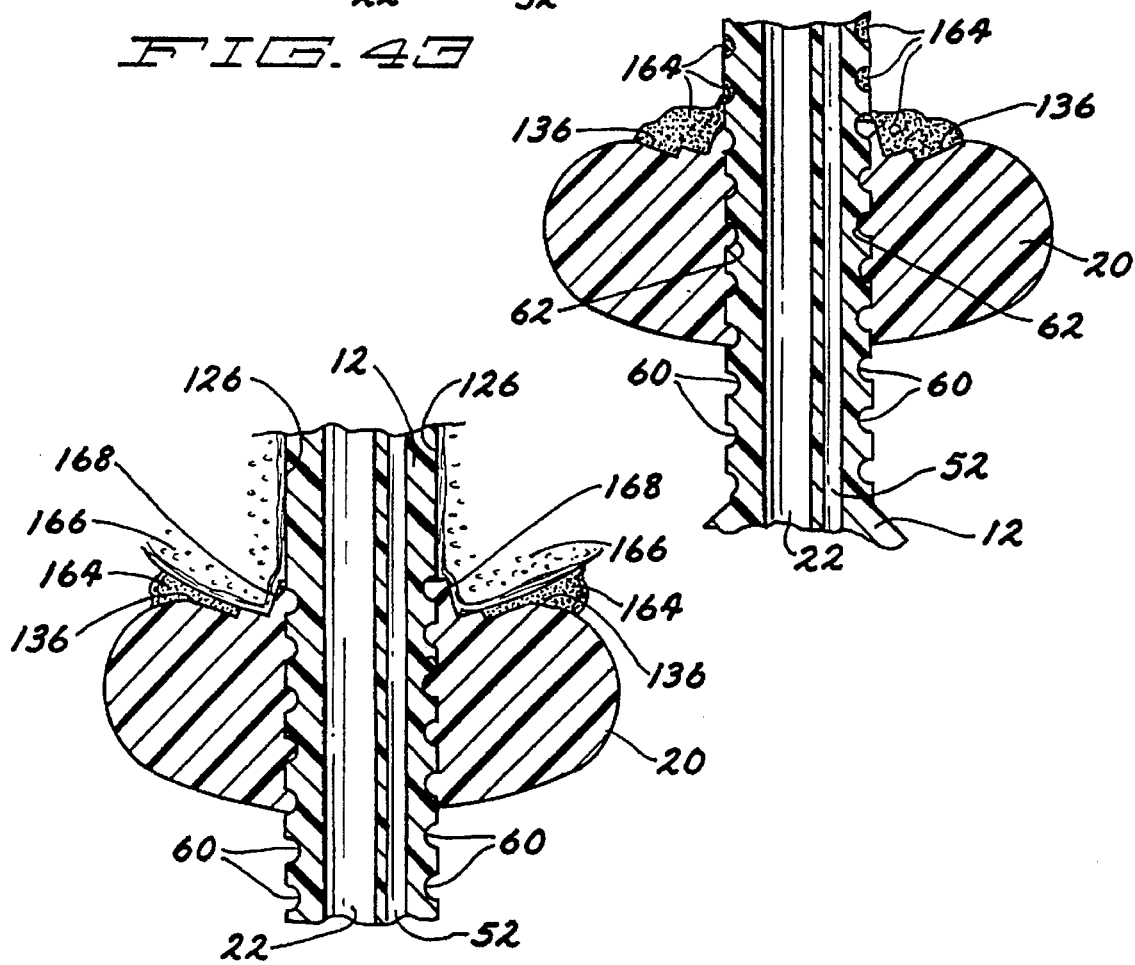
FIG. 44
FIG. 45

URINARY CATHETER HAVING PALPITATABLE VALVE AND BALLOON AND METHOD FOR MAKING SAME

BACKGROUND OF THE INVENTION

This is a continuation-in-part of application Ser. No. 08/392,529 filed on Feb. 23, 1995 now abandoned having the same title as set forth above, and for which the benefit of priority is hereby claimed pursuant to 35 USC §120.

1. Field of the Invention

This invention relates generally to catheters for controlling urinary incontinence and retention, and particularly to intra-urethral or indwelling catheters having an eternally located multiaxial palpitatable valve and an inflatable balloon disposed within the bladder of the patient.

2. Prior Art

The field of urinary catheters has long been dominated by the Foley-type catheter, which is well known in the art and comprises an inflatable balloon disposed within the patient's bladder and a discharge tube extending through the urethra to the exterior. The Foley-type catheter provides passive urinary drainage, and the ability to clamp the catheter closed at a location exterior of the patient. Representative examples of Foley-type catheters are shown in U.S. Pat. Nos. 4,055,187; 4,154,243; 4,188,954; 4,284,459; and 4,335,723 to Patel.

Foley-type catheters suffer from many drawbacks including relatively high leakage rates, the patient's inability to selectively control voiding, and the diminution in the patient's mobility or physical activities due to the need for a drainage collection device.

Several attempts have been directed towards solving these problems, and the prior art reflects that many basic improvements have been adopted and combined in a variety of forms to optimize the function of the particular catheters. However, a practical, reliable, and commercially viable alternative has not yet been achieved to meet the needs of the majority of patients.

One alternative has been direct improvements to conventional Foley-type catheters. For example, a releasable connection between the Foley-type catheter and the external drainage tube can be formed to enhance mobility, as shown in U.S. Pat. No. 4,955,858 to Drews. A check valve can also be disposed at a point along the catheter or drainage tube as shown in U.S. Pat. No. 3,967,645 to Gregory. However, these improvements do not address problems such as intra-urethral leakage, and have not resulted in a solution that is satisfactory for most patients.

The use of an inflatable balloon or other blocking device to minimize intra-urethral leakage around the exterior of the catheter, and valves disposed within the catheter body to permit selective voiding, are considered two fundamental advances in the art. Early examples of developments along these lines include U.S. Pat. Nos. 3,841,304 to Jones and 3,503,400 to Osthagen. An improvement related to the inflatable balloon or blocking device is a hydrogel collar disposed in circumscribing relations to the catheter body, designed to be moved axially along the catheter into contact with the body to hold the balloon in sealing contact with the neck and orifice of the bladder, as well as provide an additional obstacle to leakage at the distal end of the urethra.

Valves contained within the catheter that could be manipulated by bending, flexing, or extending the catheter are shown in U.S. Pat. Nos. 4,822,333 to Lavarenne; and both 4,432,757 and 4,350,161 to Davis. These types of catheters are generally unsuitable for use by female patients, and are subject to leakage resulting from normal body movement in male patients.

Collapsible- or restricted-lumen catheters that have predetermined release pressure thresholds have also been utilized. However, such devices are subject to leakage, do not drain completely, and predetermined operational pressure ranges may not be applicable to a majority of patients without undue experimentation (particularly to determine a safe high end limit to the range.) In addition, the relatively short distance between the orifice of the bladder and the distal end of the urethra in female patients limits the suitability of some designs that require an extended length of lumen to maintain the requisite pressure threshold. Representative examples of such designs are shown in U.S. Pat. Nos. 4,553,959 to Hickey and 3,672,372 to Heimlich.

Other variations unique to male or female patients have also been developed. An exterior sheath is one example of a device suitable only for male patients, as shown in U.S. Pat. Nos. 5,334,175 and 5,176,666 to Conway; 4,710,169 to Christopher; and 4,626,250 to Schneider. This type of device may be uncomfortable for some patients, and produces an increased risk of complications due to infection, interference with circulation, or impairment of reproductive functions. U.S. Pat. Nos. 5,234,409 to Goldberg; 5,114,398 to Trick; and 5,030,199 to Barwick show representative examples of valved catheters designed for female patients, and incorporating a variety of valves and actuators. These and similar devices illustrate some of the inherent obstacles in designing catheters for female patients, namely providing a manipulable or palpitatable valve that can be located and gripped by the patient without presenting a hygienic risk or being unsanitary or inconvenient for the patient to operate, as well as minimizing intra-urethral leakage on the exterior of the catheter given the relatively short length of the catheter body and catheter-to-urethra surface contact.

Another alternative has been intra-urethral plug-type devices, some of which include palpitatable or manually activated valves for selective control over voiding. These devices are generally retained within the distal end of the patient's urethra using inflatable bulbs, radial serrations, or regions of enlarged diameter, and include an exposed portion that permits selective activation of the valve or periodic removal of the device. Representative examples of such devices are shown in U.S. Pat. Nos. 5,131,906 to Chen; 5,090,424 to Simon; 4,968,294 to Salama; 4,457,299 to Cornwall; and 3,768,102 to Kwan-Gett.

A wide variety of valve designs have been contemplated for use with urinary catheters. These valves are usually actuated mechanically, but may also be actuated magnetically or by other means. The more prevalent types of mechanical valves include ball-and-seat, duckbill, inflatable check, plug, and dome-type valves. These valves may all be operated manually by the patient, however some types of valves are identified as "palpitatable" based upon a portion of the valve being squeezed or pressed in order to open the valve. The palpitatable valve may be disposed either internally or externally for male patients, although internal valves may be more difficult to use, uncomfortable, and unreliable. The palpitatable valve must be located externally for a female patient. Palpitatable valves may also be classified as orientation-dependent (uniaxial) or orientation-independent (multiaxial), based upon whether pressure must be applied to a pair of selected points or surfaces in order to open the valve sufficiently for normal operation, or whether the valve will open when pressure is exerted radially from any two opposing directions.

These basic types of mechanical, inflatable, and palpitatable valve configurations are displayed in U.S. Pat. Nos. 5,306,226 to Salama; 5,269,770 and 5,261,896 to Conway; 4,946,449 to Davis; 4,932,938 to Goldberg; 4,846,784 and 4,813,935 to Haber; and 4,643,169 to Koss, as well as several other references previously discussed. Representative examples of magnetically-actuated valves are shown in U.S. Pat. Nos. 5,041,092 to Barwick and 3,731,670 to Loe.

The Davis '449, Goldberg '938, and Haber '784 patents disclose several types of palpitatable valves that may be disposed internally or externally. A uniaxial duckbill valve may be rotated between the user's fingers until pressure is directed on the proper sites to maximize fluid flow, but the rotational torque can cause irritation, inflammation, and leakage. The Goldberg '938 patent teaches a tactile sensing means for determining the proper orientation of a duckbill valve to ensure complete opening, however properly orienting the catheter and valve upon initial insertion still requires time and training. In addition, the Davis '449 and Goldberg '938 patents both disclose dome-type valves that operate substantially the same as uniaxial duckbill valves. These dome-type valves similarly provide two opposing valve elements, but the slit or cut forming the valve opening approaches or intersects the side wall of the valve at a point below or downstream of the apex of the dome. While this configuration provides enhanced drainage capabilities for small aliquots of fluid remaining within the valve body compared with conventional duckbill valves, the proximity of the ends of the slit to the side wall of the catheter body restricts the amount that the valve can be opened in the region nearest the side wall (and therefore the lowest or most downstream portion of the valve) and risks nicking or scoring the side wall of the valve when the slit is cut. One alternative shown in the Davis '449 patent appears as a separate dome-shaped valve piece that is cut and inserted within the catheter body, which does not eliminate the restriction on the width of the valve opening adjacent the side wall of the valve body, and requires additional time, labor, cost, and quality control measures to accommodate the additional manufacturing steps.

The Davis '449 patent further shows a drainage tube connector being inserted through the dome-type valve to hold the valve in an open position. Similarly, U.S. Pat. No. 3,421,509 to Fiore discloses a protective sleeve for a urinary catheter having several overlapping wedge-shaped flap elements that are opened by insertion of a drainage tube connector.

The Haber '784 patent discloses another valve design similar in longitudinal cross section to a duckbill valve, wherein the valve elements are lobes having extended contact surfaces that present a central lumen when pressure is applied, rather than conventional blade-type elements that pivot apart when the valve is deformed.

The use of duckbill valves having pivotal blade elements or dome-type valves having single or cross-shaped slits are generally preferred for palpitatable valves, however existing catheter designs having palpitatable valves do not provide as reliable a closure under normal pressures as would be desired. In addition, the valves do not adequately drain small aliquots of urine from within the valve, thereby fostering a highly infectious environment located in close proximity to contamination from the outside environment and a pathway for ready transmission to the bladder.

The prior art patents also disclose several different balloon structures that are diagrammatically shown as generally spherical or toroidal in shape, and which seat against a substantial area surrounding the neck and orifice of the bladder. However, results using these types of balloon structures have not been highly successful. As previously noted, an unacceptable rate of leakage is still exhibited when using these balloons depending upon the underlying combination of balloon and catheter designs, the peculiarities of the particular patient's anatomy, the uniformity in fabricating the specific balloon and catheter, and the pliability or malleability of the inflated balloon. While one alternative is the use of solid, deformable, compressible, or elastic blocking members that are disposed at or within the neck of the bladder, balloon catheters are predominantly viewed as the superior choice due to their relative ease of insertion and fixation, minimum of patient discomfort, and the decreased likelihood of tissue injury or damage compared with inserting more rigid structures through confined passages.

Some solutions to the leakage problem using balloon catheters have been proposed, usually involving seating the lower portion of the balloon within the neck and orifice of the bladder to form a plug-type seal. One method for accomplishing this is to use a balloon that can be deformed by pulling downwardly on the catheter body to draw a portion of the balloon into the neck or orifice, such as shown by the Jones '304 patent. Another alternative is to inflate a portion of the balloon and catheter within the neck and orifice to form a plug-type seal. The Salama '226 patent describes a pear-shaped balloon that is inflated and the lower portion is seated within the neck and orifice of the bladder, and the Davis '938, '449, and '757 patents disclose inflating a tapered segment of the catheter wall between the balloon and a urethral cuff disposed proximate to the prostatic urethra. However, these types of designs are not believed to be particularly successful or desirable since the interior shape of the neck of the bladder varies both from patient to patient and between males and females, approaching shapes in some patients that are pyramidal rather than conical or tubular (thus preventing proper seating within the neck or orifice by a balloon having a circular radial cross section), and because inflating the balloon or catheter wall within the urethra exerts pressure that can lead to inflammation, infection, necrosis, or an unacceptable decline in tissue elasticity.

While these developments in urinary catheters have been proceeding, other ancillary improvements have also been made. For example, the Conway '770 and '896 patents disclose the use of bactericidal and microbicidal agents to prevent infection, as well as methods for the sustained release of those agents from a polymeric matrix coating or through a permeable membrane surrounding the catheter wall. The Conway '379 and '671 patents teach various manufacturing methods for coated balloon catheters and lubricated sleeves for use with those catheters.

In view of the many shortcomings and patient dissatisfaction with existing designs for urinary catheters, Applicants have therefore developed a preferred urinary catheter design intended to meet the needs and desires of the majority of male and female patients suffering from incontinence or retention disorders.

Applicants have also determined that several shortcomings presented by the prior art urinary catheter systems were not caused by inherently defective designs, but a basic misapprehension among those skilled in the art regarding the manufacturing methods that should be employed to fabricate urinary catheters and balloons that are operable for their intended purpose and consistently reliable.

For example, urinary catheters and balloons are conventionally fabricated from latex or a synthetic polymer using a multi-step dipping and curing process to form and strip successive layers of material to produce a catheter and balloon. The balloon and catheter may be formed integrally or unitarily, or may be bonded together.

However, the lack of control over the dipping, curing, and bonding processes inherently produces catheter balloons that are irregular or nonuniform in shape when inflated, or which are asymmetrically disposed relative to the catheter body. This lack of sufficient uniformity and symmetry causes intra-urethral leakage on the exterior of the catheter, whereas proper uniformity and symmetry will minimize leakage without the need for a plug-type seal within the urethra or neck of the bladder. Additional problems have been encountered with dipped catheters, such as delamination and blockages in the inflation lumen.

While dipping and curing latex catheters is the prevalent manufacturing method, it should be noted that various molding processes have been utilized in the past. U.S. Pat. Nos. 4,210,478 and 3,865,666 to Shoney and 3,959,429 to Benning disclose various methods and devices for molding a balloon onto an already-molded segment of a catheter body. The Shoney '666 patent further discloses an inverted or proximally-attached balloon that is later adhered or bonded to the catheter at its distal end. However, the processes described do not contemplate the unitary fabrication of the catheter body and balloon, thus requiring many additional manufacturing steps and subjecting the catheter body to multiple curing processes, both of which can have a detrimental effect on the uniformity and reliability of the catheter and balloon. U.S. Pat. No. 4,222,384 to Birtwell discloses molding a catheter tip and balloon as one piece to achieve an inverted balloon, however the tip and balloon must be molded or adhered to an existing catheter body. In addition, the balloon must be folded or rolled during subsequent manufacturing steps, thus increasing the complexity of the manufacturing process and the likelihood of damage to or distortion of the catheter or balloon. In contrast, U.S. Pat. No. 4,225,371 to Taylor teaches molding the balloon to the catheter body, with the unattached end of the balloon being adhered or bonded to the tip of the catheter after it is subsequently attached. As in the case of the designs discussed above, multiple manufacturing and assembly steps are required to combine and attach the various components, thereby mitigating against automated assembly, increasing the time and labor necessary to fabricate each catheter, requiring additional testing and quality-control operations, and multiplying the opportunities for and likelihood of occurrences that will diminish the reliability, uniformity, or operability of the final product. Even where the catheter tip is molded together with another portion of the catheter, additional time-consuming fabrication steps are frequently necessary to complete the catheter, such as manually punching each of the "Murphy eyes" through the proximal tip of the catheter body, a process which requires placing the catheter on a fixture, punching the eyes, removing the catheter from the fixture, and verifying the punched material has been completely excised from the catheter body.

BRIEF SUMMARY OF THE INVENTION

It is therefore one object of this invention to design an indwelling urinary catheter system of the type having: (1) a catheter body disposed within the urethra of the patient for extended periods of time, (2) a palpitatable valve that may be selectively manipulated by the patient for voiding urine, and (3) an inflatable balloon disposed within the bladder to minimize intraurethral leakage along the exterior of the catheter.

It is a related object of this invention to fabricate the above urinary catheter system using a process that optimizes the uniformity and reliability of the catheters.

It is a distinct object of this invention to fabricate the above urinary catheter system using a method that may be easily automated, in whole or in part, as desired to meet practical manufacturing and regulatory requirements.

It is another object of this invention to design the above urinary catheter system so as to incorporate a multiaxial palpitatable voiding valve which may be conveniently operated by male and female patients.

It is a related object of this invention to design the multiaxial valve such that it consistently provides a reliable closure at both low or high fluid pressures, drains completely at low or negligible fluid pressures, and permits the passage of a drainage tube connector for extended use by immobile or incapacitated patients.

It is an additional object of this invention to fabricate the above multiaxial valve using a method that enhances or enlarges the valve's seating or contact area compared with conventional duckbill or dome-type valves, and ensures that the valve elements consistently and reliably return to the proper closed configuration.

It is yet another object of this invention to design the urinary catheter system such that it may be readily adjusted to match the particular anatomical characteristics of a patient and will remain configured as adjusted, and in particular accommodates continuous incremental adjustments of the catheter length for female patients.

It is a further object of this invention to design the above urinary catheter such that the valve may be disposed externally of the patient, and wherein the exterior shape of the valve body reduces the potential for inadvertent or accidental deformation of the valve due to contact or pressure with the patient's clothing or legs, and further provides a rapid and secure connection for a drainage tube that maintains the valve in an open position.

It is yet another object of this invention to provide the above urinary catheter with the capability to adjust the pressure exerted on the inflatable balloon to a desired level to mitigate against dislodgement of the balloon.

It is still another object of this invention to provide the above urinary catheter with a reservoir for the accumulation of an antiseptic gel to form a liquid seal against the egress of urine from the urethra, and a barrier against the ingress or migration of infectious contaminants, along the exterior of the catheter.

Briefly described, the urinary catheter system of this invention includes a catheter body disposed within the urethra of the patient for extended periods of time, a palpitatable valve that may be manipulated by the patient to selectively control voiding, and an inflatable balloon disposed within the patient's bladder to retain the catheter in position and minimize leakage along the exterior of the catheter. The catheter body, tip, and balloon are molded as an integral unit using a synthetic material such as biologically compatible silicone in a manner that produces a substantially uniform balloon shape and symmetrical disposition relative to the catheter body. The balloon shape may be selectively altered by varying bonding patterns, wall thicknesses, or assembly characteristics. The catheter body is assembled with a similarly molded voiding valve. The palpitatable valve preferably includes a multiaxial dome-type construction with a peripheral trough surrounding the dome adjacent to and displaced slightly from the wall of the valve body. The peripheral trough maximizes drainage and permits a wider valve opening. In the preferred embodiment, each valve element is separated from adjacent valve elements by an intermediate rib, and the valve elements and intermediate ribs may be readily displaced radially from the longitudinal axis of the valve by insertion of a drainage tube connector. The valve elements are formed by cutting the dome while deformed to a flat configuration to create seating surfaces that are angled to increase their contact area. A retention collar is positioned on the catheter body for female patients and may be adjusted axially along helical threads to exert the desired level of tension on the catheter body to maintain the balloon in contact with the interior wall of the bladder adjacent the neck and orifice. The catheter and balloon may be fabricated using a bactericidal-containing synthetic resin, coated with bactericidal or friction-reducing agents, or the balloon may be inflated with a bactericide-treated fluid that permeates the balloon. An antiseptic gel coating the threaded portion of the catheter accumulates on the proximal face of the retention collar and forms a fluid seal and barrier against migration of infectious contaminants along the exterior of the catheter, with a conical portion of the retention collar optionally being received within the distal orifice of the urethra.

BRIEF DESCRIPTION OF THE DRAWINGS

FIG. 43 is a partial cross section view of the threaded portion of the catheter body with the retention collar in the most distal position, with an antiseptic gel received within the threads of the catheter body;

FIG. 44 is a partial cross section view of the threaded portion of the catheter body with the retention collar disposed between the most distal and most proximal positions, with the antiseptic gel received accumulating on the proximal face of the retention collar;

FIG. 45 is a partial cross section view of the threaded portion of the catheter body with the retention collar in the most proximal position closely adjacent an area of tissue surrounding the distal orifice of the urethra, with the antiseptic gel forming a fluid seal and a barrier to the migration of infectious contaminants along the exterior of the catheter body through the distal orifice of the urethra, with a conical portion of the retention collar partially received within the distal orifice of the urethra;

DESCRIPTION OF THE PREFERRED EMBODIMENTS

The urinary catheter of this invention is shown in FIGS. 1–49 and referenced generally therein by the numeral 10.

Figure 1:
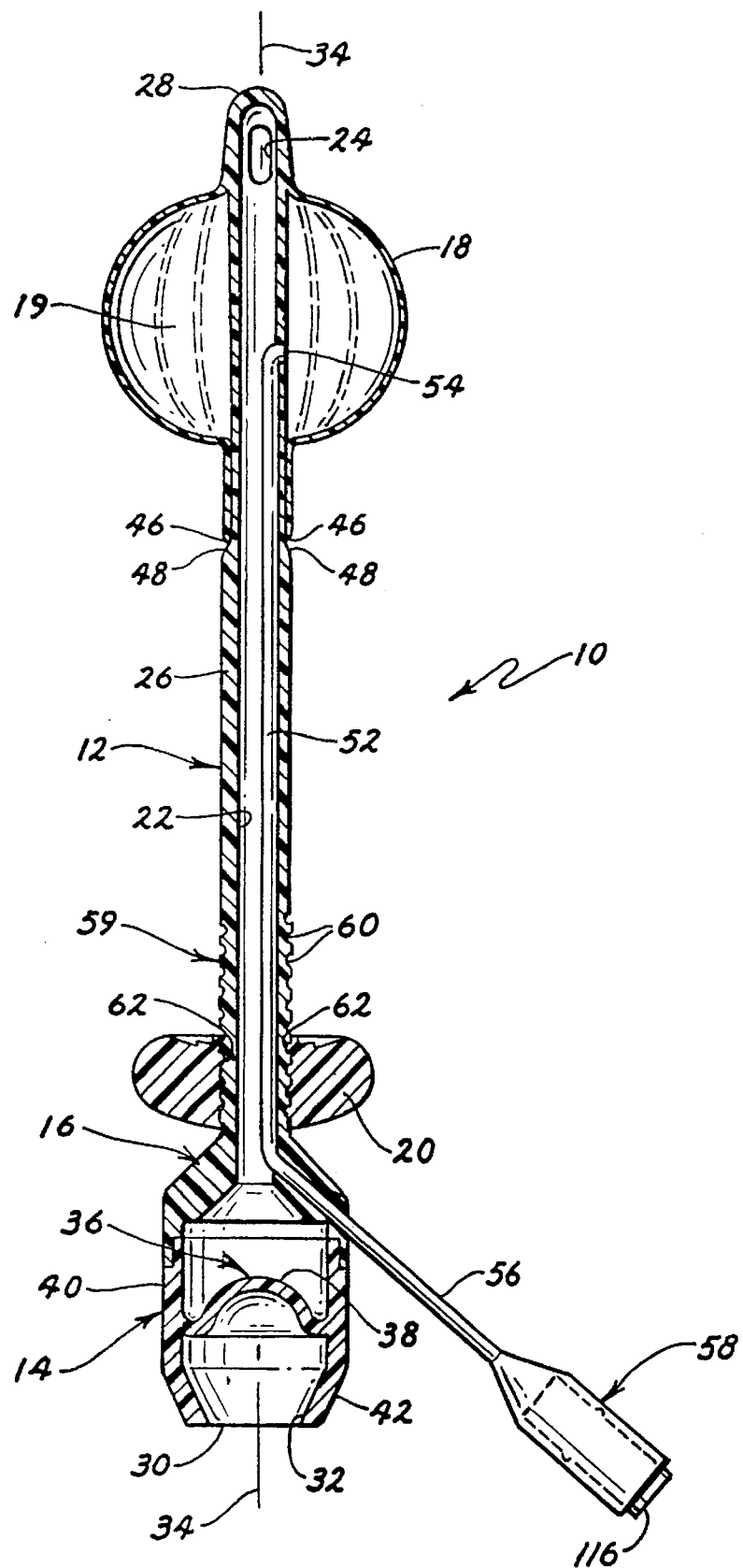
FIG. 1 is a longitudinal cross section view of the urinary catheter of this invention.
Figure 2:
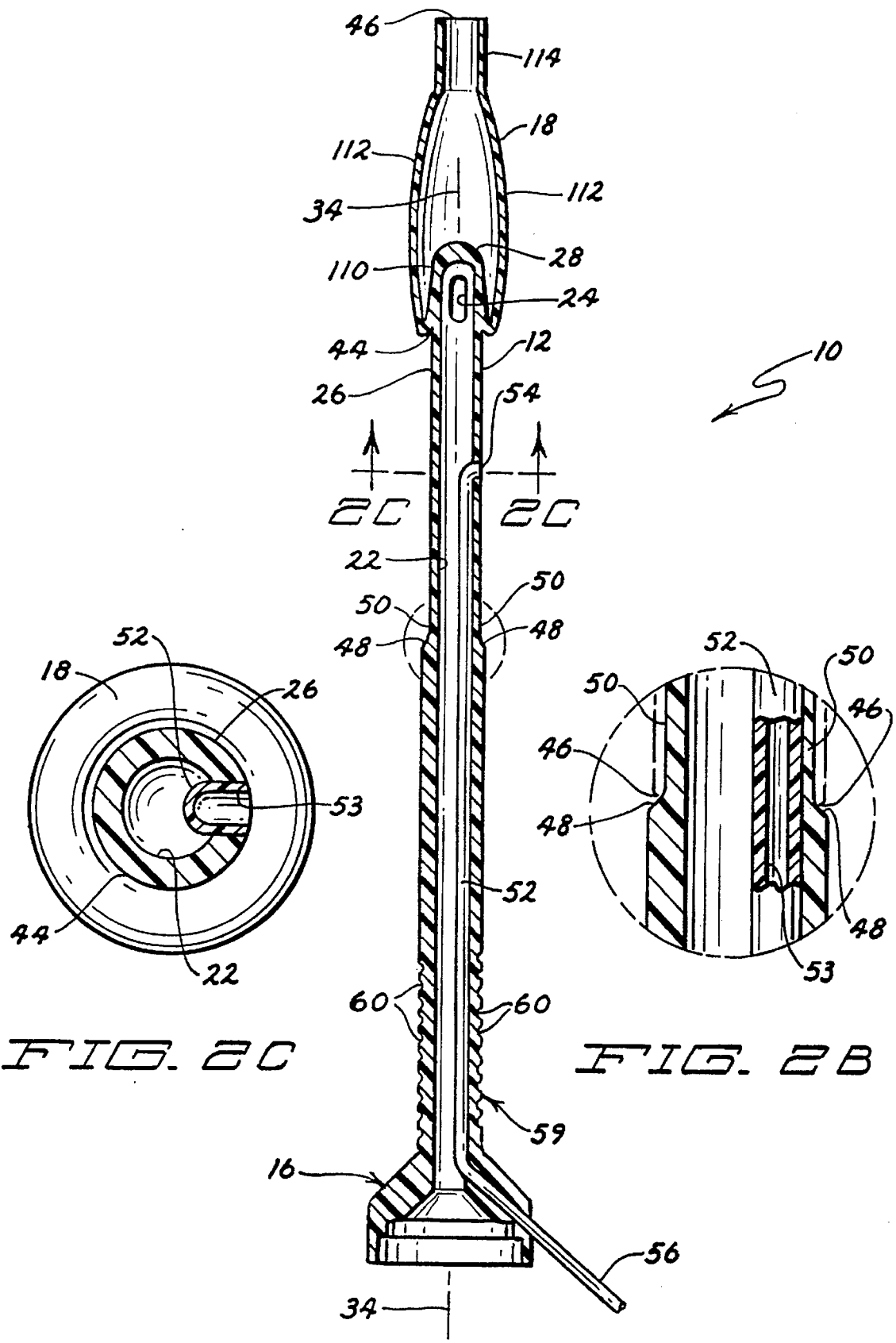
FIG. 2A is a longitudinal cross section view of the proximal portion of the catheter of FIG. 1, showing the distal end of the inflatable balloon inverted relative to the catheter body.
FIG. 2B is an enlarged detail view of a segment of the proximal portion of the catheter body shown circled in phantom in FIG. 2A.
FIG. 2C is a proximally-directed cross section view of the catheter body taken through line 2C–2C in FIG. 2A.
Figure 3:
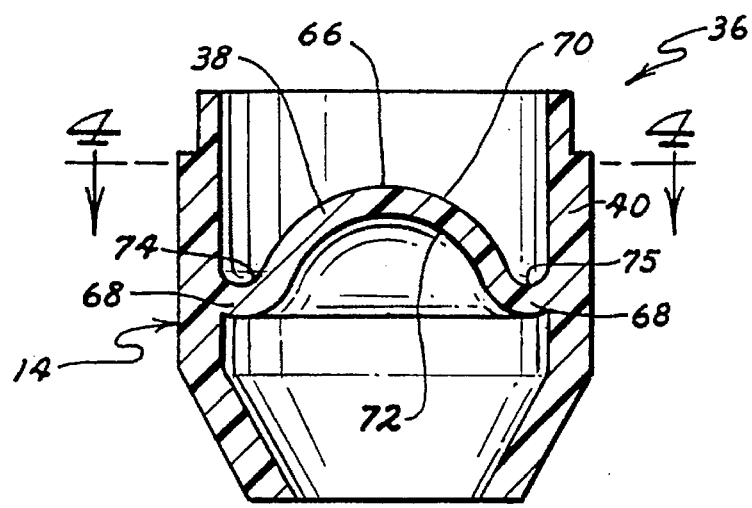
FIG. 3 is a cross section view of the distal portion of the catheter body of FIG. 1 showing the intact configuration of the dome-type voiding valve.

Referring particularly to FIGS. 1–3, it may be seen that the catheter 10 includes a catheter body 12 that is composed of a distal portion 14 and a proximal portion 16 that are matingly connected as described below. An inflatable balloon 18 is connected to and extends from the catheter body 12, and a retention collar 20 is disposed in circumscribing relation on the catheter body 12.

The catheter body 12 defines a central lumen 22 extending from and communicating with an opening 24 through the side wall 26 of the catheter body 12 closely adjacent the proximal end 28 of the catheter body 12 to the distal end 30 of the catheter body 12 which defines a voiding opening 32. The proximal end 28 of the catheter body 12 preferably forms a partially enclosed and rounded tip of the catheter body 12, with the exception of the opening 24. The catheter body 12 and central lumen 22 thereby define a longitudinal axis 34 extending along the entire length of the catheter body 12, although the catheter body 12 may be freely flexed out of alignment with the longitudinal axis 34. A plurality of openings 24 may also be utilized, including an opening 24 which intersects or overlaps the longitudinal axis 34 at the tip 28 of the catheter body 12.

The distal portion 14 of the catheter body 12 defines a multiaxial palpitatable valve 36 preferably including a dome-type valve member 38 that may be moved between a normally closed position and an open position when the patient grips and deforms the valve 36 by applying squeezing pressure against any two opposing sides of the valve wall 40, which also forms the side wall of the distal portion 14 of the catheter body 12.

The valve wall 40 is generally cylindrical at its proximal end, and at its distal end defines a truncated conical segment 42 having an inward radial taper terminating in the voiding opening 32. The proximal end of the distal portion 14 of the catheter body 12 defines a segment of reduced outer diameter in the valve wall 40 that permits the proximal end of the distal portion 14 to be matingly and engagingly received within and fixedly connected to the distal end of the proximal portion 16 of the catheter body 12, with the distal end of the proximal portion 16 correspondingly defining a segment of increased inner diameter, with the distal portion 14 and proximal portion 16 having the same outer diameter so as to form a flush outer surface having a generally cylindrical shape coextensive between the distal portion 14 and proximal portion 16 of the catheter body 12.

The inflatable balloon 18 is connected to and molded unitarily at its proximal end 44 with the proximal portion 16 of the catheter body 12 including the catheter tip 28, and is initially configured such that the distal end 46 of the inflatable balloon 18 is displaced from the catheter body 12 in an inverted configuration with the inflatable balloon 18 extending in the proximal direction away from the catheter body 12 and circumscribing the longitudinal axis 34, with a substantial portion of the balloon 18 being disposed more proximally relative to the tip 28 of the catheter body 12 as shown particularly in FIG. 2.

The catheter body 12 defines an inwardly tapered neck 48 having a diameter reduced an amount corresponding approximately to the thickness of the inflatable balloon 18, so that the inflatable balloon 18 is folded dismally until the distal end 46 contacts the tapered neck 48 and a seating region 50 along the exterior of the catheter wall 26 immediately adjacent and proximal to the tapered neck 48, with the distal end 46 of the inflatable balloon 18 being adhered to the exterior surface of the catheter wall 26 along a portion of the seating region 50 so as to form a flush outer surface having a generally cylindrical shape coextensive between the outer surface of the inflatable balloon 18 and the catheter wall 26. A fluid-tight seal is therefore formed between the inflatable balloon 18 and the catheter wall 26 to enclose an interior region within the inflatable balloon 18.

An inflation lumen 52 is defined within the catheter wall 26 extending from an opening 54 in the catheter wall 26 communicating with the interior of the inflatable balloon 18 to an intermediate tube 56 and inflation port 58 extending radially outward from the proximal portion 16 proximal to the connection to the distal portion 14. The inflation lumen 52 is similarly molded as an integral component of the proximal portion 16 of the catheter body 12, with the inflation lumen 52 sharing the side wall 26 of the catheter body 12 as a common wall throughout the coextensive portion of those components. Fluid is injected through the inflation port 58 and inflation lumen 52 to inflate the inflatable balloon 18 from a completely collapsed configuration through an intermediate configuration shown in phantom in FIG. 1, to a completely inflated yet highly pliable or compliant configuration, which may be either a generally spherical shape as shown in FIG. 1 that is both radially and axially symmetrical, or conversely a toroidal or axially asymmetrical shape as described in further detail below.

The catheter wall 26 defines helical threads 60 along a portion of the exterior surface, with the collar 20 defining mating threads 62 which permit the collar 20 to be moved in infinitesimal increments axially up or down the catheter body 12 by rotation of the collar 20 relative to the catheter body 12.

Figure 4:
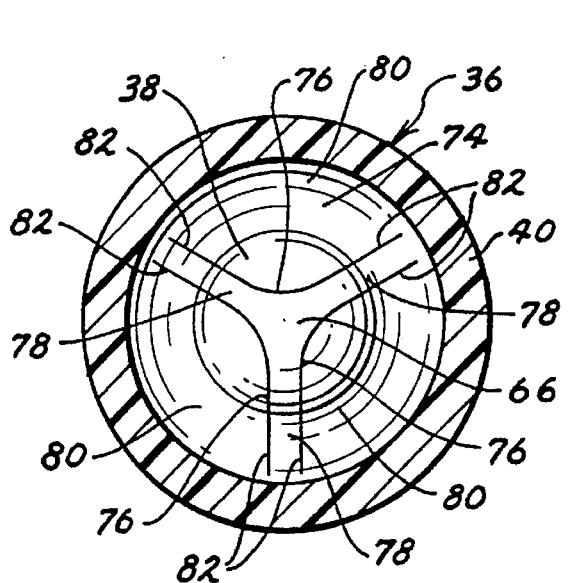
FIG. 4 is a top cross section view of a preferred embodiment of the voiding valve taken through line 4—4 in FIG. 3 showing the valve in the relaxed and closed position.
Figure 5:
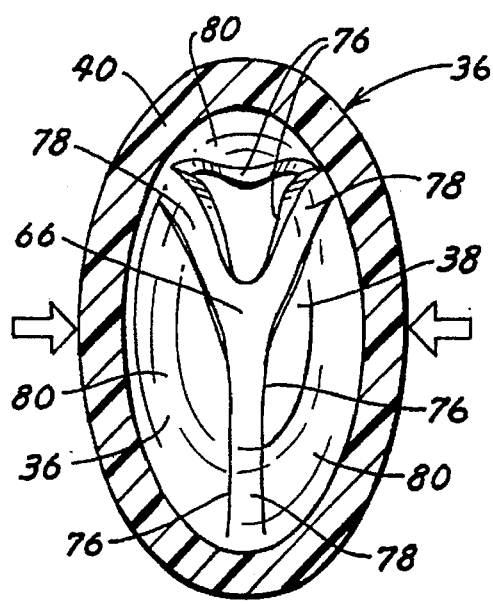
FIG. 5 is a top cross section view of the voiding valve of FIG. 4 showing the valve in the deformed and open position.

Referring particularly to FIGS. 1 and 3–5, a preferred embodiment of the dome-type valve 36 is shown. The valve member 38 has a generally circular shape in axial cross section as shown in FIGS. 4 and 5, and an arcustc shape in longitudinal cross section as shown in FIGS. 1 and 3. The valve member 38 extends radially inward and slightly distally downward from the interior surface of the valve wall 40, and then further radially inward and generally proximally upward to an apex 66 intersecting the longitudinal axis 34, thereby forming a trough or intermediate region 68 circumscribing a generally arcuate central dome having a convex surface 70 facing generally proximally or upstream opposing the flow of fluid, a concave surface 72 facing generally distally or downstream, and a peripheral edge 74 generally defined by and along a path connecting the most distal points along the convex surface 70 of the valve member 38.

The valve member 38 defines three arcuately curved valve openings 76 cut entirely through the surface thereof, the valve openings 76 being displaced from one another so as to form three intermediate ribs 78 connected to one another in a central location to form a Y-shape and separating three valve segments 80 from one another. When the valve wall 40 is squeezed radially inward from any two diametrically opposing sides, such as shown by the hollow arrows in FIG. 5, the valve wall 40 and valve member 38 are deformed substantially from the closed configuration shown in FIGS. 3 and 4 to an open configuration as shown in FIG. 5. At least one element 80 of the arcustc dome 38 flexes proximally or upstream, and the boundaries of the valve openings 76 defined by the contacting surfaces between the valve segments 80 and intermediate ribs 78 separate to dispose one or a plurality of openings through which fluid may flow through the interior of the valve 36 and the voiding opening 32. When the radially inward pressure is released, the valve 36 returns to the closed configuration shown in FIGS. 3 and 4, with the edges or contact surfaces of the valve segments 80 contacting the closely confronting surfaces of the intermediate ribs 78 to maintain proper alignment and closure of the valve openings 76 without the valve segments 80 overlapping or being axially displaced so as to present a gap through which fluid could drain.

The cuts or slits through the valve member 38 forming the valve openings 76 extend from the their highest respective point on the arcuate dome 38 downwardly or distally and intersect with the peripheral edge 74, which demarks the lowest or most distal points or path along the convex surface 70 of the valve member 38. These intersection points 82 between the valve openings 76 and the peripheral edge 78 of the dome are disposed at or near the radial center of trough or intermediate region 68 at approximately the lowest or most distal point, with the entire upstream surface of the valve member 38 being disposed more proximal than those intersection points 82, thereby ensuring that when the valve openings 76 are in the open configuration the valve member 38 will not present any concave recesses disposed more proximal to the intersection points 82, and fluid within the interior of the valve 36 will drain completely through the valve openings 76 even though there is little or substantially no remaining fluid pressure.

It may be appreciated that a variety of surface configurations and non-uniform terrains may be utilized for the convex surface 70 and concave surface 72 of the valve member 38, however it is preferred that in any such configuration no portion of the upstream face of the trough or intermediate segment 68 along the shortest path from an intersection point between the valve opening 76 and the peripheral edge 74 and the adjacent or most proximate portion of the valve wall 40 be disposed further downstream than that intersection point, thereby preventing an aliquot of fluid from being trapped in a recess or cavity rather than draining through the valve opening due to the force of gravity when the valve member 38 is deformed and the valve 36 is maintained in the open position. In this preferred embodiment, that arcuate segment or dome of the valve member 38 defines a generally uniform ovoid section extending downwardly to the peripheral edge 74, with the peripheral edge 74 defining a plane oriented generally perpendicular to the longitudinal axis 34 of the catheter body 12 within the interior region of the valve 36.

In addition, the slits defining the valve openings 76 may extend from the arcuate dome 38 across the peripheral edge 74 toward the interior surface of the side wall 40, but preferably not actually contacting or intersecting the interior surface of the side wall 40. In this manner, the width of the valve opening 76 is increased in the region directly adjacent to or surrounding the intersection points 82 between the valve openings 76 and the peripheral edge 74 (representing the bottom-most point of the trough or intermediate section 68) compared with the width of a conventional valve opening 76 at the intersection with the side wall 40 of the valve 36. The result is to increase low-pressure drainage compared with conventional dome-type valves, and minimize the risk that the side wall 40 will be damaged during fabrication of the valve openings 76. This also increases the eventual maximum width of the valve openings 76 at the greatest distances from the side wall 40 when the dome 38 is fully deformed. Given a predetermined separation between the peripheral edge 74 of the valve member 38 and the side wall 40, the valve opening 76 could extend from the valve member 38 past the intersection points 82 a distance on the order of one half that separation.

Figure 16:
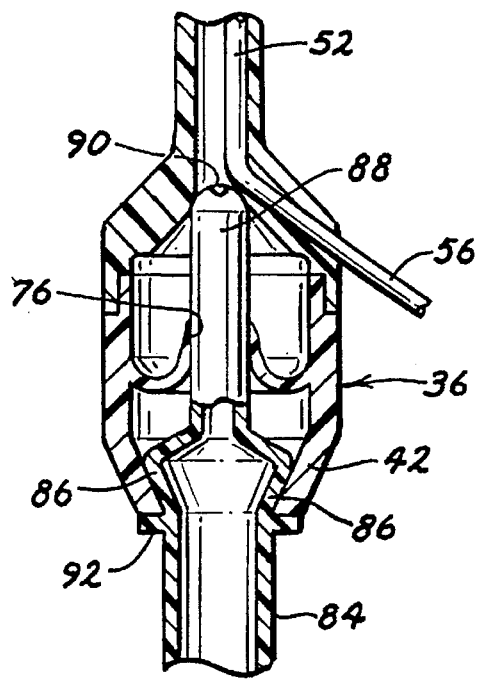
FIG. 16 is a cross section view of the lower portion of the catheter body of FIG. 1 with a drainage tube connecter inserted through the valve element.

The particular configuration of the valve member 38 shown in FIGS. 1 and 3–5 permits use of the catheter 10 with a drainage tube connector 84 as shown particularly in FIG. 16. The drainage tube connector 84 includes a tapered neck 86 sized and shaped to fit and engage within the truncated conical segment 42 of the valve 36 and thereby be retained against axial movement or inadvertent disconnection. The proximal end of the tapered neck 86 has a generally hollow stent tube 88 that radially displaces the intermediate ribs 78 as the stent tube 88 is inserted through the valve member 38, and extends proximally through one of the valve openings 76 and into the distal end of the central lumen 22. The proximal end of the stent tube 88 preferably engages the side walls 26 of the central lumen 22, disposing an aperture 90 in fluid communication with the central lumen 22. This frictional engagement resists inadvertent or unintentional disconnection of the drainage tube connector 84 from the valve 36, and further ensures that fluid does not leak around the periphery of the stent tube 88 into the interior of the valve 36. The valve elements 80 and intermediate ribs 78 return to the closed and sealed position when the stent tube 88 is removed along with disconnection of the drainage tube connector 84. A radial shoulder 92 on the drainage tube connector 84 prevents overinsertion of the stent tube 88.

Figure 9:
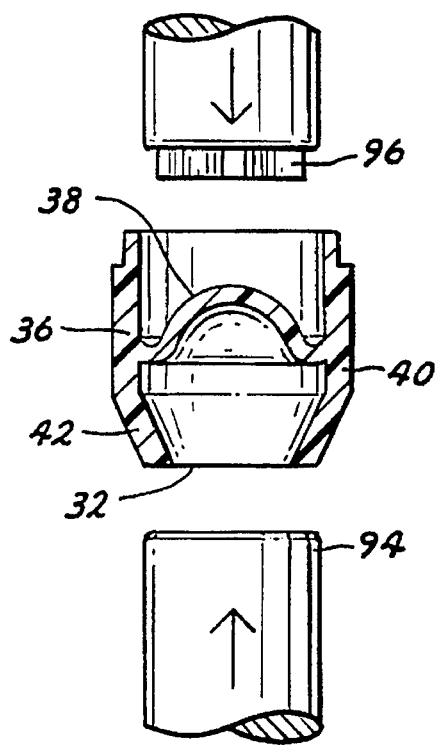
FIG. 9 is a diagrammatic cross section view of the valve with the mandril and cutting tool displaced therefrom.
Figure 10:
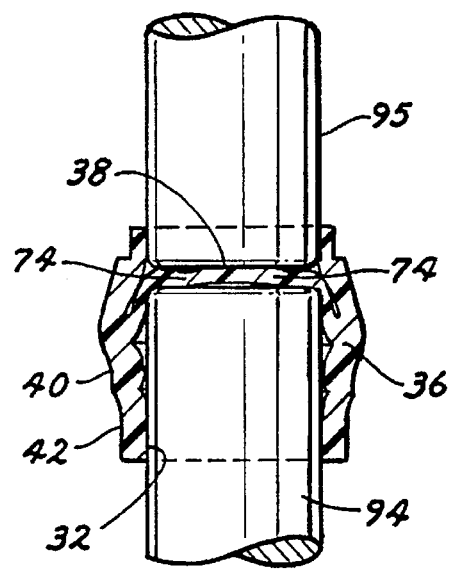
FIG. 10 is a diagrammatic cross section view of the valve with the mandril and cutting tool disposed within the interior of the valve and the valve element deformed.

Referring particularly to FIGS. 9 and 10, it may be seen that the valve openings 76 are cut through the valve member 38 by inserting a radially oversized mandril 94 through the voiding opening 32 of the valve 36, thereby flexing the truncated conical segment 42 outward and stretching the valve wall 40 and valve member 38 radially outward and away from the longitudinal axis until the valve member 38 is in a generally planar or flat configuration as shown in FIG. 10, compared with the normally convoluted and arcuate configuration shown in FIG. 9. A cutting tool having a blade member 96 on its leading edge is inserted through the proximal opening in the distal portion 14 of the valve 36, and into close proximity to the valve member 38. Using opposing pressure exerted by the mandril 94 to restrain the valve member 38 against axial movement, the blade member 96 is forcibly pressed toward the mandril 94 so that the blade member 96 contacts and completely penetrates the valve member 38 and defines the particular pattern or configuration of valve openings 76 that is desired. The top surface of the mandril 94 is fabricated from a sufficiently compliant material such that the blade member 96 may score the surface of the mandril 94 to ensure complete penetration of the valve member 38. The cutting tool 96 and mandril 94 are removed from the interior of the valve 36, which is released from the stretched position so that the valve member 38 returns to its normally undeformed convoluted configuration as shown in FIG. 9. The truncated conical section 42 of the valve 36 may initially be stretched to permit ingress of the mandril 96 using a plurality of fingers (not shown) or other segments that are inserted within the valve 36 through the distal opening 32 and are separated to stretch the valve 36 sufficiently to permit passage of the mandril 94. The fingers or other segments may be removed during the cutting operation to maintain uniform radial tension on the valve member 38. It may further be noted in FIG. 10 that in the deformed configuration, the valve member 38 may be stretched across the top and down the sides of the mandril 94, with the generally flat or planar section corresponding to the area of the valve member 38 within and defined by the peripheral edge 74 and encompassing the portion of the intermediate section 68 or trough disposed within the peripheral edge 74. In an embodiment where the valve openings 76 cross the peripheral edge 74 and extend beyond the lowest point of the trough or intermediate region 68, the mandril 94 must be slightly larger than the diameter of the peripheral edge 74. It may be appreciated that the valve member 38 may not achieve a completely flat or planar configuration, since tension decreases proportionately to the proximity to the center point or longitudinal axis 34 of the valve member 38, however the blade member 96 presses the valve member 38 substantially flat prior to cutting.

Figure 11:
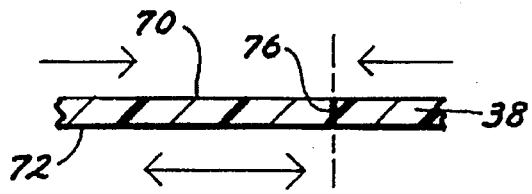
FIG. 11 is a diagrammatic cross section view of a segment of the valve element in the deformed configuration showing the cut.
Figure 12:
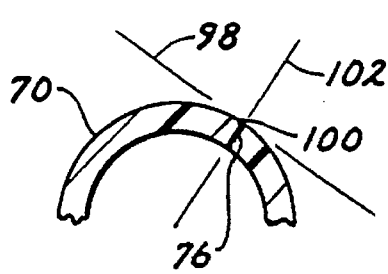
FIG. 12 is a diagrammatic cross section view of a segment of the valve element in the relaxed configuration showing the cut.
Figure 13:
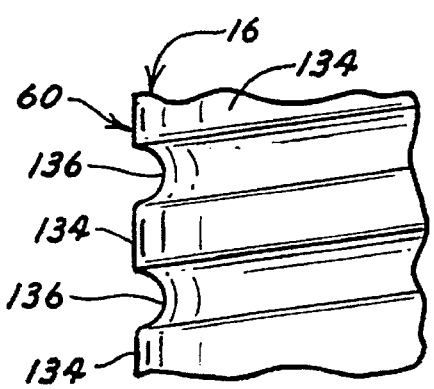
FIG. 13 is a detail view of the lands and grooves of the helical threading of the catheter body of FIG. 1.

The process of deforming the valve member 38 to a generally planar configuration produces compressive forces along the normally convex surface 70, and tensile forces along the normally concave surface 72, as shown by the force arrows in FIG. 11. When the valve member 38 is cut perpendicularly in the deformed configuration as shown in FIGS. 10 and 11 and then released to the unstressed and convoluted configuration as shown in FIG. 12, the cut forming the valve opening 76 has two confronting and contacting faces. The shortest straight line path for these faces is defined by a line 102 generally perpendicular to and bisecting a plane 98 disposed tangentially to the intersection point 100 of the convex surface 70 and the cut forming the valve opening 76. Due to the compressive and tensile forces and the density and malleability of the material from which the valve member 38 is fabricated, the cut forming the valve opening 76 may traverse a slightly curved or arcuate path rather than a straight line path, and the angle of the cut line 76 relative to the normal line 102 may also vary slightly as the path of the valve opening 76 is traversed from one end to the other. If the cut forming the valve opening 76 is oriented at an angle relative to the normal line 102, the cut will have an effective depth greater than the normal thickness of the valve member 38, thereby increasing the contact area between the confronting faces of the valve segments 80 (or valve segment 80 and intermediate rib 78) compared with a cut extending through the valve member 38 normal or perpendicular to its surfaces 70, 72 along line 102.

In the three-element 80 valve 36 with intermediate ribs 78 shown in FIGS. 4 and 5, the top valve member 38 deforms upwardly and is displaced a greater radial and axial distance than the intermediate ribs 78 or lower two valve elements 80. When pressure is released, the intermediate ribs 78 and lower two valve elements 80 return to their original closed configuration prior to the top valve element 80, which subsequently nests and seats properly against the intermediate ribs 78 as the valve element 80 moves radially and axially back into contact with the intermediate ribs 78.

Figure 7:
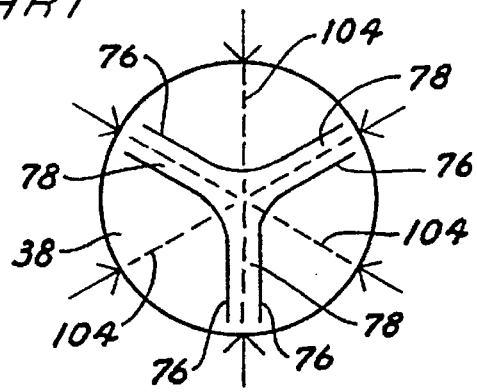
FIG. 7 is a diagrammatic top plan view of a preferred embodiment of the dome-type valve having three equilateral valve elements and three centrally connected intermediate ribs forming a Y-shape.

Referring to FIGS. 4, 5, and 7, it may be appreciated that pressure applied to opposing sides of the valve 36 as shown in FIG. 5 may be oriented along any one of three equilateral-spaced diametric axes 104 to open one of valve elements 80 substantially upward and shift the remaining valve elements 80 and central connection of the intermediate ribs 78 slightly upward and radially in the opposite direction away from the valve element 80 that opens upward. Conversely, pressure applied from opposing sides but disposed between two of the axes 104 will partially deform a pair of valve elements 80 and valve openings 76 proportionately to the angular separation between the adjacent axes 104 and the source of pressure, thereby providing approximately the same total flow area.

Figure 6:
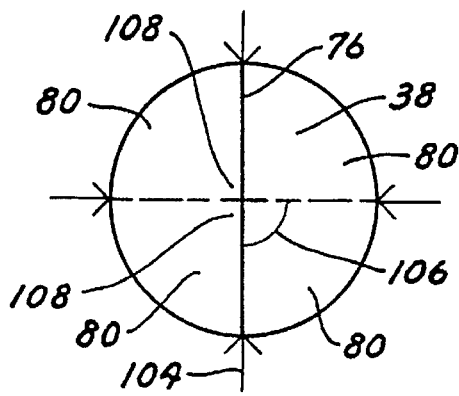
FIG. 6 is a diagrammatic top plan view of a dome-type valve having a first straight slit and a second straight slit in phantom oriented perpendicular to the first straight slit.
Figure 8:
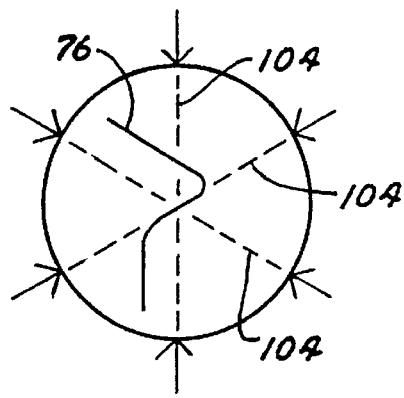
FIG. 8 is a diagrammatic top plan view of an alternate embodiment of the dome-type valve having a serpentine slit.

Referring to FIGS. 6–8, it may be appreciated that the selection of a preferred configuration for the valve openings 76 or slits and the valve elements 80 in a dome-type valve 36 depends upon balancing several factors 3A the hardness, curvature, and thickness of the material at various locations on the valve element 80 (affecting the "memory" of the valve element 80 and the force, speed, and consistency with which it returns to the original closed position), the relative length and width of the valve element 80, the number of the valve elements 80, and their respective orientation along contact or seating surfaces.

Referring to FIG. 6, a single slit or valve opening 76 placed along the diameter of the valve member 38 produces a pair of valve elements 80 and a single axes 104. This valve 36 configuration has been referred to herein as a uniaxial valve 36, since pressure must be applied at two opposing surfaces in a set orientation, such as with a duckbill valve. Adding a second slit (shown in phantom in FIG. 6) perpendicular to the first valve opening 76 produces four valve elements 80 and essentially four valve openings 76 that intersect as a single passage. The number of axes 104 increases to two, but the angle 106 between the adjacent edges of the valve elements 80 along the valve openings 76 decreases to approximately 90° ¾ thereby weakening the memory of the valve elements 80 at the points 108 and increasing the likelihood that the valve elements 80 will overlap or not seat properly when the valve 36 closes.

Figure 20:
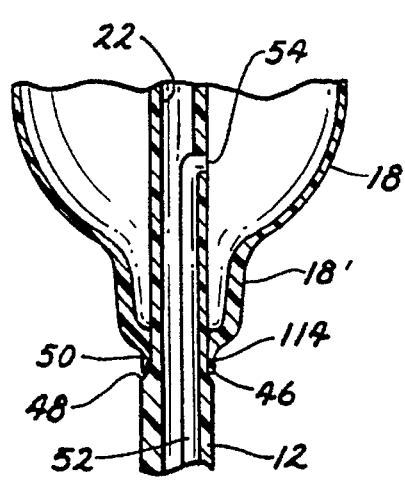
FIG. 20 is a side cross section view of the upper portion of the catheter body and generally toroidal balloon of FIG. 18, wherein the base of the balloon forms a generally cylindrical stepped segment having a diameter greater than that of the catheter body and less than the maximum diameter of the balloon.
Figure 21:
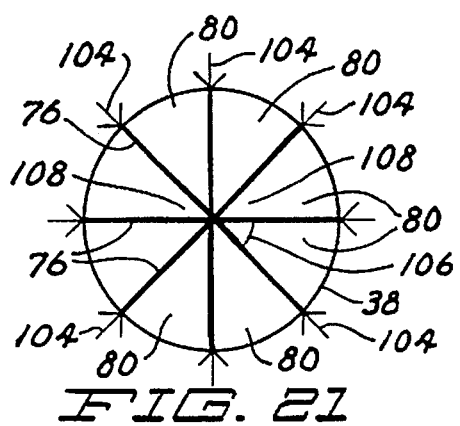
FIG. 21 is a diagrammatic view of a dome-type valve having four diagonal slits and eight valve elements.
Figure 22:
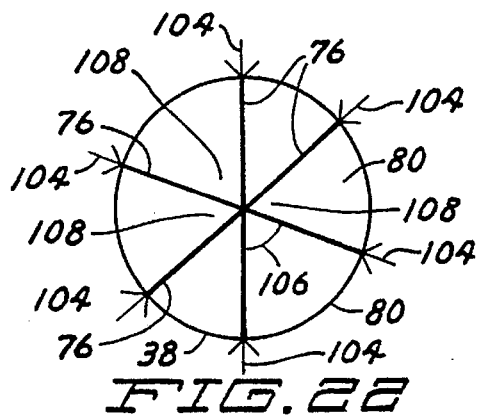
FIG. 22 is a diagrammatic view of a dome-type valve having three diagonal slits and six valve elements.

Increasing the number of diametric slits to four as shown in FIG. 21 increases the corresponding number of valve openings 76 and valve elements 80 to eight, as well as the number of axes 104 to four, but decreases the angle 106 to 45° and produces a very significant decline in the memory of the valve elements 80 adjacent to the points 108 relative to the configuration shown in FIG. 20. This results in a valve that can easily be deformed and provides good multiaxial characteristics, but closes slowly or incompletely, and allows the valve elements 80 to "catch" and overlap one another adjacent the points 108 so that the valve 36 leaks significantly. Decreasing the number of diametric slits to three as shown in FIG. 22 decreases the corresponding number of valve openings 76 and valve elements 80 to six, as well as the number of axes 104 to three, but increases the angle 106 to 60° and increases the memory characteristics of the valve elements 80 adjacent to the points 108.

Figure 23:
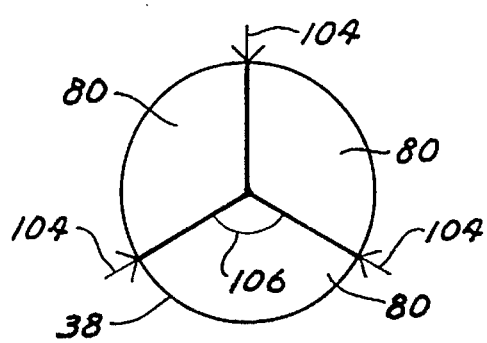
FIG. 23 is a diagrammatic view of a dome-type valve having three equilateral slits that intersect at a central point and form three valve elements.

One alternative is to provide a valve 36 with valve openings that do not cross the valve member 38 diametrically, as shown in FIG. 23. For example, a valve member 38 defining three radial slits joined at the center point produces three valve openings 76 and three equilateral-spaced axes 104, with an angle 106 of 120° formed at the points 108. Continuing the progression suggests that the lower number of slits and valve elements 80 the greater the angle 106 at the points 108 and the better the memory characteristics. However, the final step results in a valve 36 with a single slit forming one valve opening 76 with no points 108, but with uniaxial orientation along a single axis 104 as shown in FIG. 6.

Figure 24:
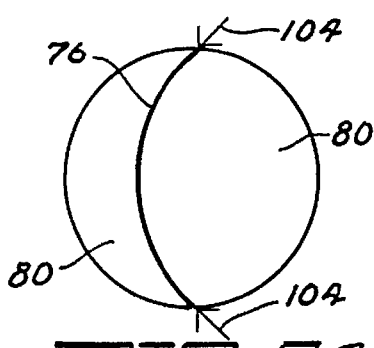
FIG. 24 is a diagrammatic view of a dome-type valve having one curved slit intersecting the diameter of the valve at the ends thereof to form two valve elements.

However, it may also be appreciated that the effective number of axes 104 defined by a valve 36 having a single slit and one valve opening 76 may be increased by curving the slit or valve opening 76 as shown in FIG. 24. Pressure applied to opposing surfaces of the valve will open the portion of the valve opening 76 which extends generally parallel with the axes 104 connecting the two pressure points. Stated conversely, segments of the slit or valve opening 76 define lines or axes 104, and pressure applied to opposing points along a line parallel to these axes 104 will cause that segment of the valve opening 76 to open.

Figure 35:
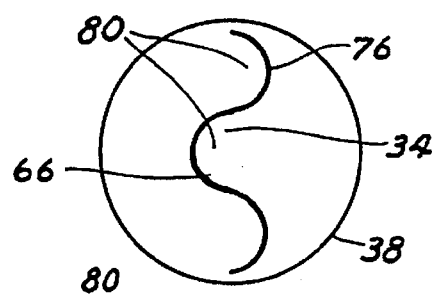
FIG. 35 is a diagrammatic view of a dome-type valve having one serpentine slit defining three curves of generally equal radii, with one central curve overlapping the center point of the valve.

It may be appreciated that a valve 36 having multiple axes 104 may be fabricated using a single continuous slit or valve opening 76 if that slit or valve opening 76 traverses a "serpentine" pathway as shown in FIGS. 8 and 35, with discrete segments of the valve opening 76 being orientated generally parallel with the axes 104 along which pressure is applied from opposing aides of the valve 36. The "true" number of axes 104 is actually defined by the number of discrete segments of the valve opening 76 that are oriented at divergent angles and together form a composite serpentine curve, however for purposes of simplicity the axes 104 aligned with the various curved segments of the valve opening 76 have been discounted. As such, the axes 104 indicated become the "major" or "primary" axes 104 responsible for deforming and opening a significant portion of the valve member 38 in normal operation. Orientation of these "primary" axes 104 at three equilateral positions produces a suitable multiaxial valve 36 for the application described herein. In is understood that curved slits or valve openings 76 such as those shown in FIGS. 4, 7, and 24–33 may also be considered "serpentine" in the sense that they traverse arcuate paths and present a multiplicity of axes each parallel to a segment of the slit, with the axes 104 parallel to the ends of the slits usually constituting the major or primary axes 104.

Figure 25:
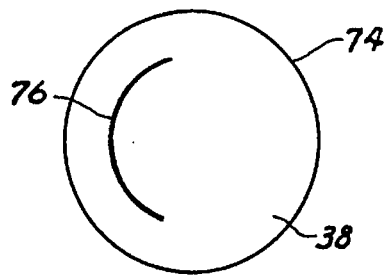
FIG. 25 is a diagrammatic view of a dome-type valve having one curved slit that does not intersect the diameter of the valve at the ends thereof and forms two valve elements.
Figure 26:
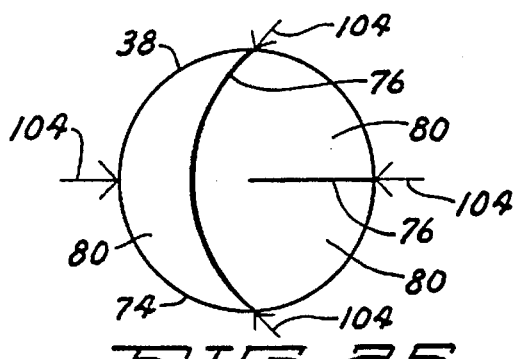
FIG. 26 is a diagrammatic view of a dome-type valve having one curved slit that intersects the diameter of the valve at the ends thereof and a straight slit that does not intersect the curved slit and forms three valve elements.
Figure 27:
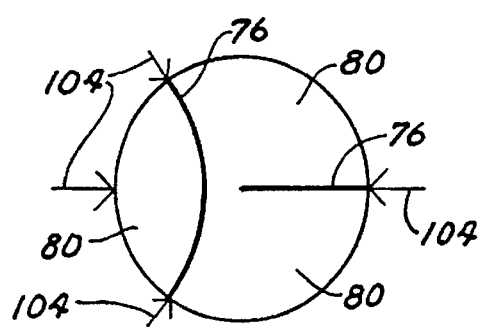
FIG. 27 is a diagrammatic view of a dome-type valve as in FIG. 26 with the orientation of the curved slit reversed.
Figure 28:
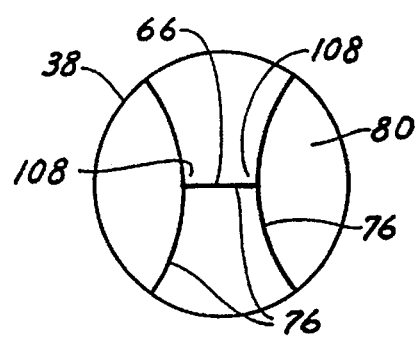
FIG. 28 is a diagrammatic view of a dome-type valve having two curved slits that are connected at their midpoints by a straight slit to form four valve elements.
Figure 29:
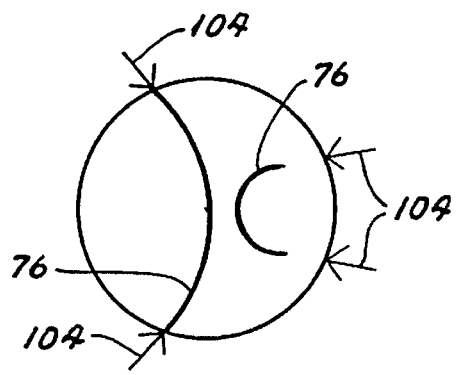
FIG. 29 is a diagrammatic view of a dome-type valve having two curved slits of differing radii that do not intersect.
Figure 30:
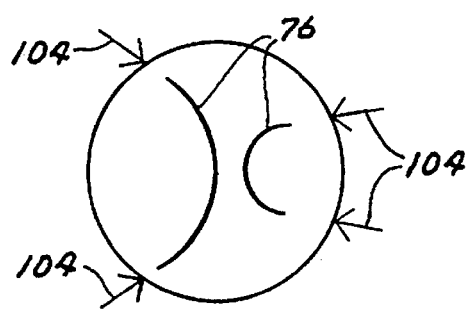
FIG. 30 is a diagrammatic view of a dome-type valve having two curved slits of differing radii which do not intersect each other as in FIG. 29, but one of which intersecting the peripheral edge.
Figure 31:
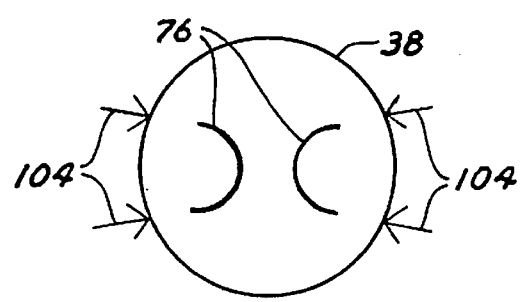
FIG. 31 is a diagrammatic view of a dome-type valve having two curved slits of generally equal radii that convexly confront and are spaced apart from one another.
Figure 32:
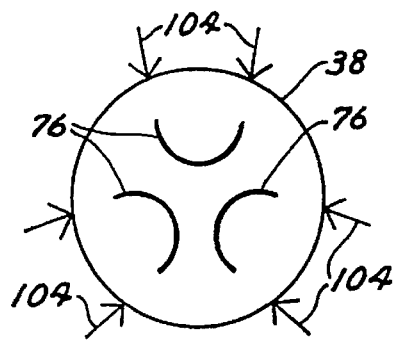
FIG. 32 is a diagrammatic view of a dome-type valve having three curved slits of generally equal radii that convexly confront and are equidistantly spaced apart from one another.
Figure 33:
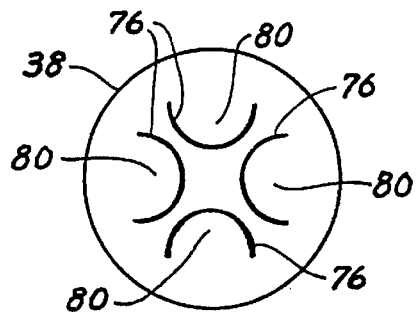
FIG. 33 is a diagrammatic view of a dome-type valve having four curved slits of generally equal radii that convexly conform and are equidistantly spaced apart from one another.
Figure 34:
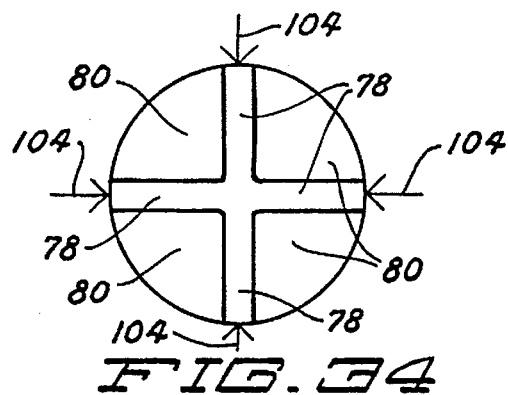
FIG. 34 is a diagrammatic view of a dome-type valve having four curved slits that convexly confront one another to form four valve elements separated by four intermediate ribs that intersect and are joined in a central region.

It may be readily appreciated that the configurations of dome-type valves 36 described herein may be categorized into three groups: straight-slit valve openings 76 (as shown in FIGS. 6 and 21–23; valve openings 76 defining intermediate ribs 78 (as shown in FIGS. 4, 5 and 7); and serpentine valve openings 76 (as shown in FIGS. 8 and 24). However, the variety and complexity in the combinations of these valve openings 76 can increase. For example, FIG. 25 shows a single valve opening 76 comprising a single radially-offset curved slit that does not intersect the peripheral edge 74 of the valve member 38. FIG. 26 shows a curved slit defining a first curved valve opening 76 intersecting the peripheral edge of the valve member 38, and a straight slit defining a second valve opening 76 having an axis 104 oriented acutely to both axes 104 of the curved valve opening 76. This configuration may be considered to produce two valve openings 76 with three valve elements 80. In FIG. 27, the orientation of the curved valve opening has been reversed so that the ends of the valve opening 76 do not intersect diametrically opposed points on the peripheral edge 74 of the valve member 38. FIG. 28 includes two curved valve openings 76 connected at their center points by a straight valve opening 76 that bisects the apex 66 of the valve member 38, thereby forming four valve elements 80 having centrally located points 108. FIGS. 29 and 30 show two potential orientations of a valve 36 having two curved valve openings 76 each of different radii, and increasing the number of available axes 104. FIGS. 31–33 show three potential configurations for equidistantly-spaced curved valve openings 76 of approximately equal radii. It may be appreciated that the configuration shown in FIG. 32 approaches the configuration of the valve 36 shown in FIGS. 4 and 7, having three valve elements 80, three valve openings 76, and three intermediate ribs 78. Similarly, the configuration shown in FIG. 33 approaches the configuration of the valve 36 shown in FIG. 34, having four valve elements 80, four valve openings 76, and four intermediate ribs 78. While the valve 36 shown in FIG. 33 would effectively have three primary axes 104 spaced equidistantly or equilateral, the valve 36 shown in FIG. 34 has only two perpendicular axes 104. Finally, a configuration for a serpentine valve 36 is shown in FIG. 35 that provides two or three valve elements 80 using a single valve opening 76, depending upon how one differentiates the two adjacent valve elements 80 on the left-hand side of the FIG. 35, and wherein the center valve element 80 overlaps or encompasses the apex 66 and longitudinal axis 34 of the valve member 38, thereby providing a section of the valve member 38 that may be easily displaced by insertion of the stent tube 88 of a drainage tube connector 84.

The use of curved slits and intermediate ribs 78 produces a synergistic effect by providing a multiaxial valve 36 that will seat reliably and completely, and eliminating sharp corners that can overlap or catch due to poor memory in the adjacent portions of the valve elements 80.

It should be noted that the preferred valve 36 has been described herein as having a dome-type valve member 38, however this representative terminology can include a variety of other types of valve members 38 having corresponding shapes such as conical, truncated conical, oval or ovoid, pyramidal, trapezoidal. The common element among these configurations of valves 36 is their inclusion of an elevated region disposed more proximally and forming an apex 66, and a surrounding lower portion disposed more distally and forming a base or peripheral edge 74 which may gradually and uniformly transition into a trough or intermediate region 68.

Referring again to FIG. 2, it may be seen that the proximal portion 16 of the catheter body is molded with the inflatable balloon 18 formed integrally or as an integral part connected to and extending from the catheter body 12 at the proximal end 44, with the distal end 46 and substantially all of the inflatable balloon 18 being disposed proximally relative to the proximal end 44 of the inflatable balloon 18 in an "inverted" configuration. The partially enclosed and radiused proximal tip 110 at the proximal end 28 of the catheter body 12 is also formed integrally with the proximal portion 16 of the catheter body 12 and inflatable balloon 18. The inflatable balloon 18 is initially disposed in a tubular form, with a slight bulge or curvature to the intermediate segments 112 of the side walls of the inflatable balloon 18, and a generally cylindrical seating segment 114 disposed adjacent to and overlapping the distal end 46 of the inflatable balloon 18. This initial bulge or curvature decreases the pressure necessary to initiate inflation, and lowers the eventual maximum inflation pressure needed to achieve a particular inflated shape so that the inflatable balloon 18 remains softer, more pliable, and yet stronger and more resistant to failure when fully inflated. The exterior of the catheter body 12 adjacent the proximal end 44 of the inflatable balloon 18 may be roughened or patterned to prevent the inflatable balloon 18 from adhering to any surface of the catheter body 12 it might contact prior to or during curing, when removed from the mold, or during subsequent handling.

The inflatable balloon is folded distally until the distal end 46 is adjacent to and contacting and engaging the inwardly tapered neck 48 of the catheter body 12. The distal end 46 of the inflatable balloon 18 is fixedly and sealingly attached to the catheter body 12 using an adhesive bond between a predetermined portion of the seating segment 114 and the exterior surface of the catheter body 12 within the seating region 50. The length of the bond within the seating segment 114 measured between its proximal and distal ends, and the distance between the distal end 48 or tapered neck 48 and the most proximal end of the bond within the seating segment 114 will selectively determine or affect the shape of the inflatable balloon 18 when it is partially and fully inflated. For example, extending the bond proximally can produce an axially asymmetrical balloon shape. The ultimate shape and axial symmetry of the inflatable balloon 18 when inflated will depend upon the length of the inflatable balloon 18 between its proximal 44 and distal 46 ends, the thickness and uniformity of the intermediate segments 112 of the side walls of the inflatable balloon 18, and the length, position, displacement, and uniformity of the bond within the seating segment 114.

Referring to FIGS. 14, 15, 18, and 19, it may be appreciated that the axial (and radial) symmetry or asymmetry of the inflatable balloon 18 may be affected in a controlled manner by altering the thickness of the proximal end 44, distal end 46, or intermediate segments 112 of the side walls of the inflatable balloon 18 and the inflation pressure to form a virtually limitless variety of shapes and configurations. Some more conventional shapes may include toroidal (axial length greater than radial diameter), spheroidal (axial length equalling radial diameter), toroidal (radial diameter greater than axial length), pear (proximal end radially larger than distal end), and tear (distal end radially larger than proximal end.)

Figure 14:
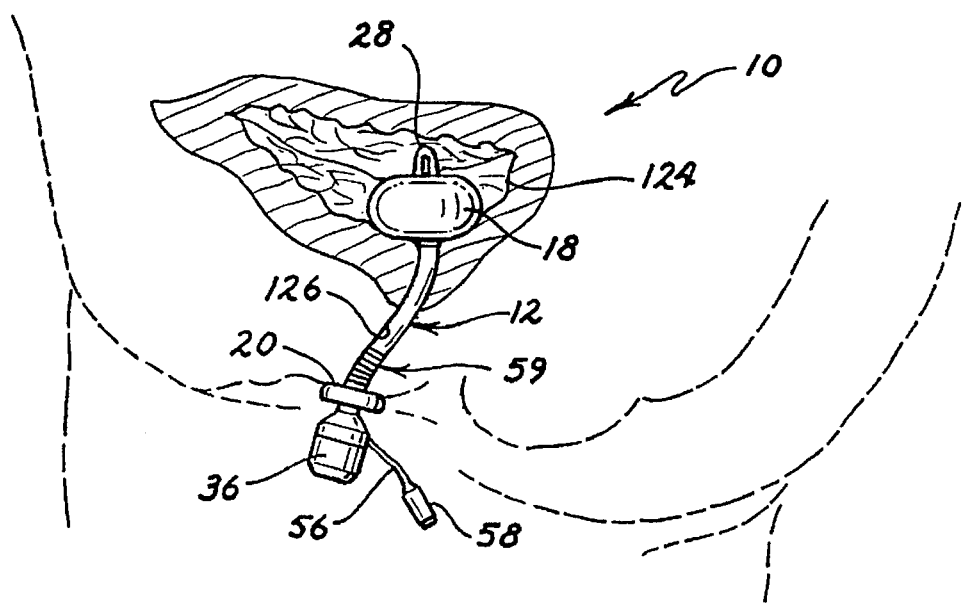
FIG. 14 is an anatomical side section view of the urinary tract of a female patient showing the catheter of this invention implanted therein, the catheter having a toroidal balloon and a retaining collar.
Figure 15:
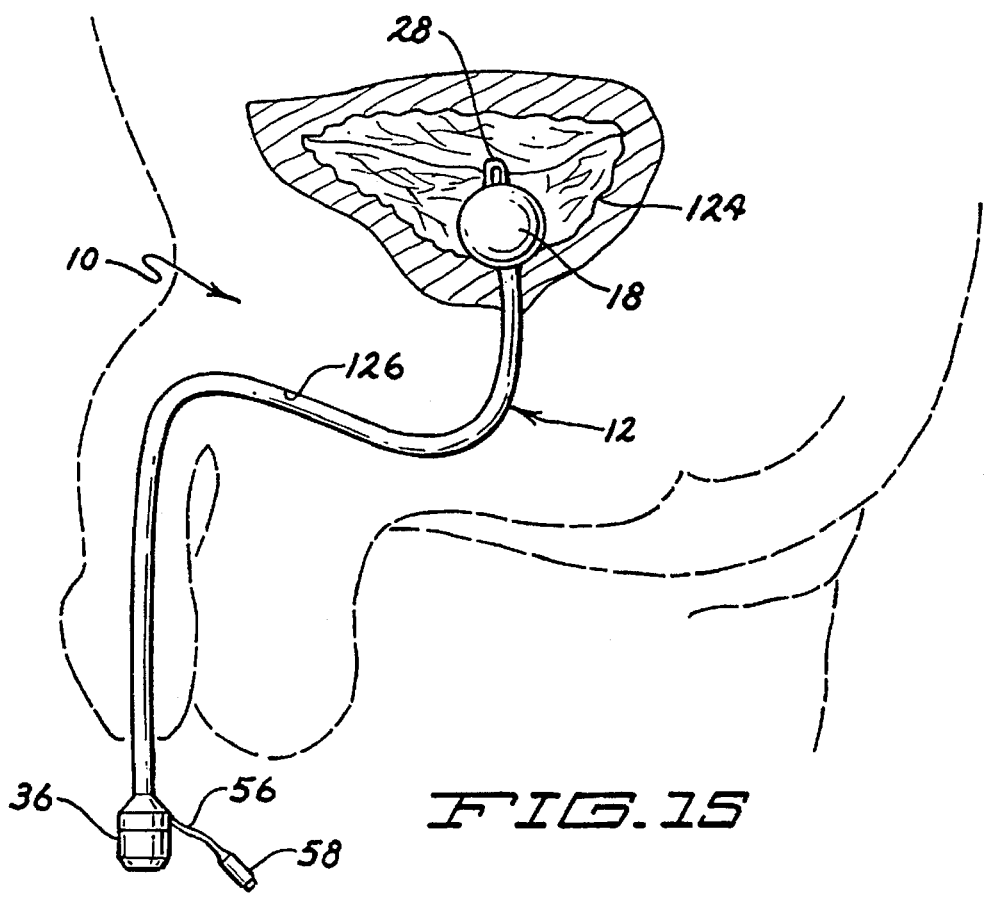
FIG. 15 is an anatomical side section view of the urinary tract of a male patient showing the catheter of this invention implanted therein, the catheter having a generally spherical balloon.
Figure 18:
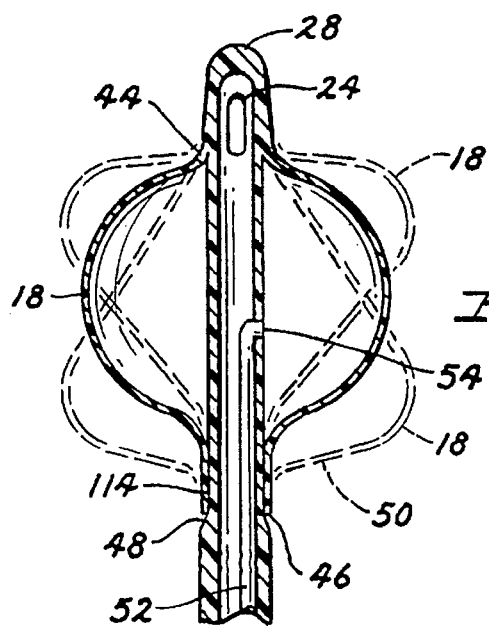
FIG. 18 is a side cross section view of the upper portion of the catheter body and generally spherical balloon of FIG. 1, with two alternate embodiments of the balloon shape shown in phantom.
Figure 19:
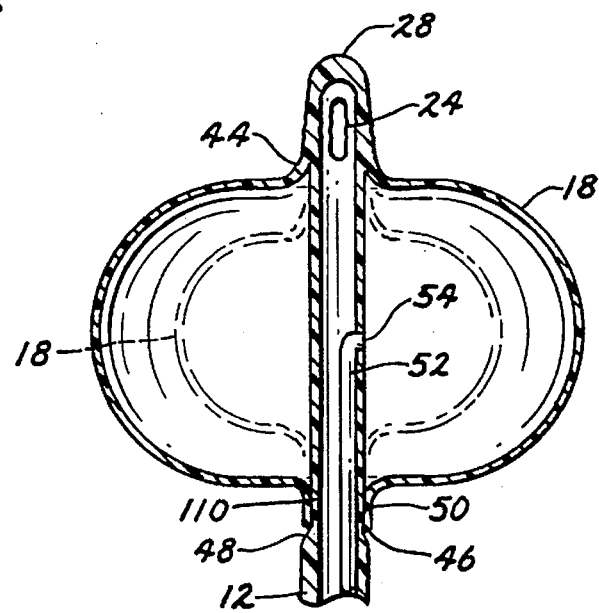
FIG. 19 is a side cross section view of the upper portion of the catheter body and generally toroidal balloon of FIG. 14, with one alternate embodiment of the toroidal balloon shape shown in phantom.

A generally spherical configuration for the inflatable balloon 18 is believed preferable for male patients as shown in FIGS. 15 and 18. Conversely, a toroidal shape is believed preferable for female patients as shown in FIGS. 14 and 19. The toroidal shape may be accomplished by inflation of the inflatable balloon 19 to a generally toroidal shape, or as shown in phantom by increasing the wall thicknesses of the inflatable balloon adjacent the proximal end 44 and distal end 46 (as well as increasing the length of the bond between the seating segment 114 and seating region 50) to produce a toroidal effect.

Referring to FIG. 18, a combination of increasing the wall thickness of the inflatable balloon 18 in selected regions and adjusting the length and placement of the bond between the seating segment 114 and seating region 50 can be utilized to produce axially asymmetrical configurations for the inflatable balloon 18, such as are shown in phantom in FIG. 18.

Referring particularly to FIG. 20, more complex shapes such as a stepped configuration for the inflatable balloon 18 may be achieved by varying the wall thickness of the inflatable balloon 18 and the length and placement of the bond between the seating segment 114 and seating region 50. In the stepped configuration of FIG. 20, a first region of the inflatable balloon 18' has a slightly thicker wall than the remainder of the inflatable balloon 18, resulting in a generally cylindrical region of decreased diameter compared with the uniform curvature of a spherical balloon 18 when inflated. The potential shapes and configurations for the inflatable balloon 18 which may be achieved are virtually limitless given different thicknesses of the wall of the inflatable balloon 18, patterns of varying thickness that can be molded into the interior or exterior surfaces of the inflatable balloon, the bonding pattern, and the inflation pressure. It may be readily appreciated that the molding and bonding processes described will permit configurations, orientations, and varying wall thicknesses for an inflatable balloon 18 that cannot be achieved using conventional dipping, masking, and stripping processes known to the art.

It should be noted that the inflatable balloon 18 is initially formed with the intermediate segments 112 of the side walls slightly curved or bowed to minimize the inflation pressure initially required to induce inflation. Some physicians may prefer this configuration for insertion of the catheter body 12, whereas others may prefer to draw a vacuum and retract the inflatable balloon 18 to a completely deflated and collapsed configuration (not shown).

In the preferred embodiment, the inflatable balloon 18 has either a generally spheroidal or generally toroidal shape in which the thickness of the side walls of the inflatable balloon 18 is substantially uniform along each path circumscribing the inflatable balloon 18 formed at each axial segment along the longitudinal length of the inflatable balloon 18, and over the entire surface area of the inflatable balloon 18, such that the inflatable balloon 18 is uniformly and symmetrically shaped and disposed in radial symmetry relative to the longitudinal axis 34 of the catheter body 12.

Figure 36:
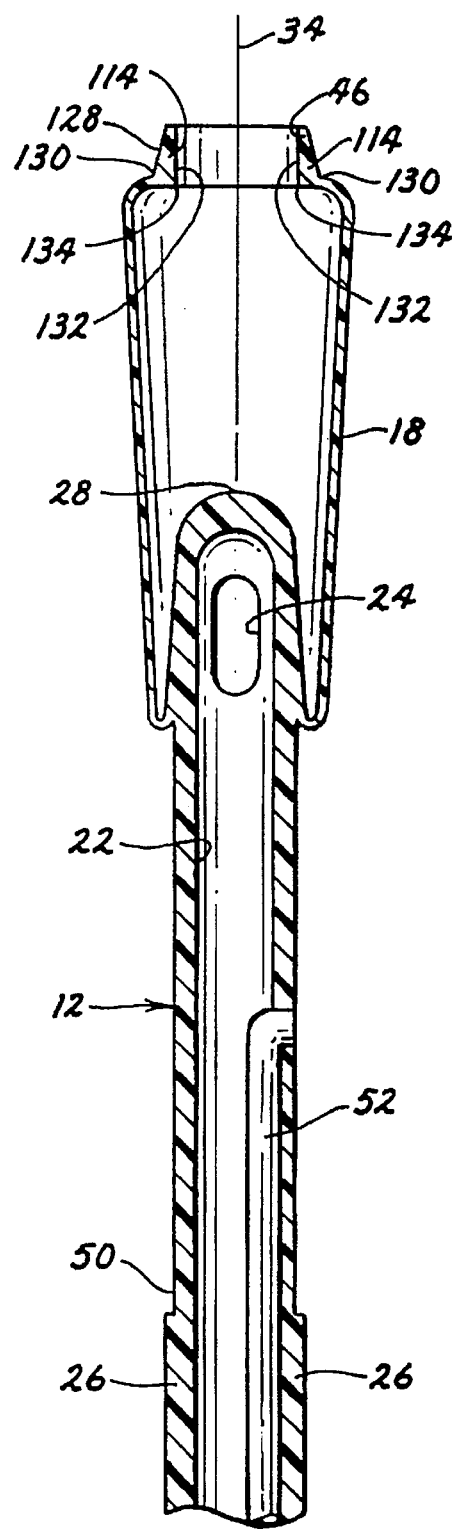
FIG. 36 is a partially broken away side cross section view of an alternate embodiment of the inflatable balloon and catheter body of this invention with the balloon in the inverted configuration.
Figure 37:
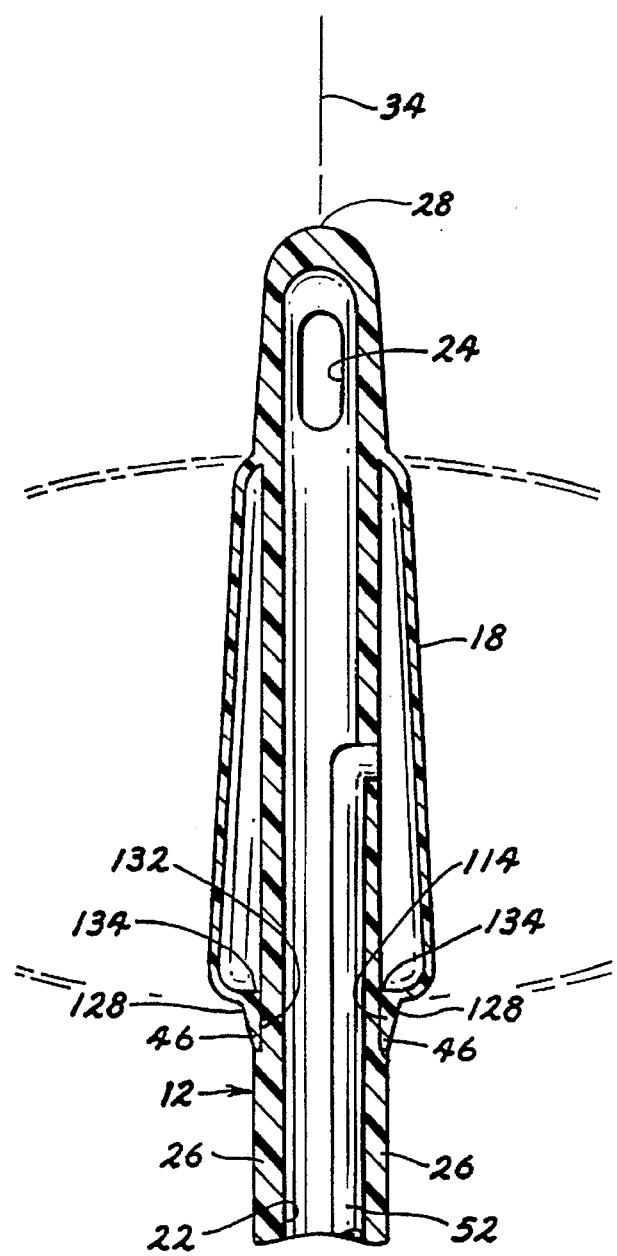
FIG. 37 is a partially broken away side cross section view of the alternate embodiment of the inflatable balloon and catheter body of FIG. 36 with the projecting segment forming a truncated conical surface extending radially from the catheter body adjacent the distal end of the balloon.

Referring to FIGS. 36 and 37, it may be appreciated that an alternate embodiment of a toroidal shape inflatable balloon 18 may be molded such that the distal end 46 of the inflatable balloon 18 defines a tapered segment 128 throughout the length of the cylindrical seating segment 114, such that the outer surface forms an angular junction 130 with at bottom of the inflatable balloon 18 along the exterior, and the inner surface 132 remains generally parallel with the surface of the catheter body 26 to provide a bonding surface. The inner surface 132 similarly forms an angular junction 130 with the inflatable balloon 18, such that the inflatable balloon 18 extends from the tapered segment 128 at an angle generally perpendicular to the longitudinal axis 34 of the catheter body 26. The tapered segment 128 thereby forms a noninflatable truncated conical sealing member that may be received within the neck or orifice of the bladder 124 to further minimize leakage, but which does not change its shape or diameter when the inflatable balloon 18 is inflated and also does not affect the otherwise toroidal or spherical shape of the inflatable balloon 18 when in the fully inflated configuration. Because the tapered segment 128 and angular junctions 130, 134 orient the wall of the inflatable balloon 18 towards perpendicular to the longitudinal axis 34 of the catheter body 26 at the bottom of the balloon 18, the tapered segment 128 and angular junctions 130, 134 ensure that the bottom annular surface of the inflatable balloon 18 contacting the bottom wall of the bladder 124 will be generally coplanar and parallel with the inner horizontal surface of the bladder 124 surrounding the neck and orifice of the bladder 124. However, it should be noted that this embodiment increases the effective diameter of the catheter body 26 when the inflatable balloon 18 is initially deflated for insertion through the urethra 126.

Other complex shapes for the inflatable balloon 18 may also be produced using the molding process involving varying wall thicknesses and initial configurations. For example, it is anticipated that one useful configuration would be a balloon having a "mushroom" or "umbrella" shape, oriented in either an upright or inverted configuration with the catheter body 26 as the stem or handle, that is radially symmetric but has axially overlapping portions. Another useful configuration would include "projections" or "fingers" that extend radially outward and axially at a distal or proximal angle relative to the catheter body 26, providing an inflatable anchoring configuration similar to that produced by mechanical or articulated anchors described in the prior art. The advantages of such configurations include decreased inflation volumes, lower inflation pressures, smaller seating areas adjacent the neck and orifice of the bladder 124 (to reduce instances where drainage or normal movement of the bladder 124 causes contact between the inflatable balloon 18 and wall of the bladder 124 that would otherwise dislodge the inflatable balloon 18), more pliable side walls of the inflatable balloon 18 that would prevent contact with the wall of the bladder 124 from a transverse radial direction from placing undue axial tension on the catheter body 26 due to pivoting of the inflatable balloon (causing both leakage and pain to the patient), and to promote increased drainage and retraction of the bladder 124.

Figure 17:
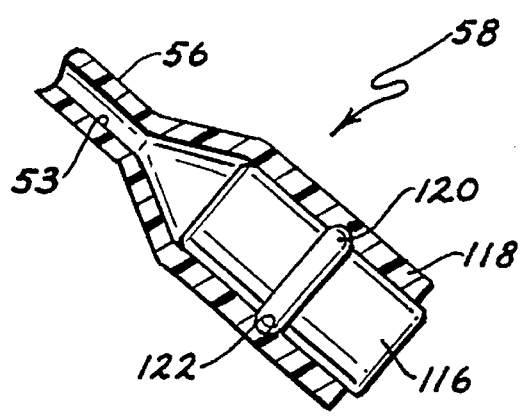
FIG. 17 is a partially broken away cross section view of one embodiment of the inflation port.

Referring to FIGS. 1 and 17, it may be seen that the injection port 58 is fabricated by inserting or receiving a conventional Halkey-Roberts type valve 116 into a molded retainer 118 attached in fluid communication with the intermediate tube 56 and inflation lumen 52. The Halkey-Roberts type valve 116 may have the retainer 118 molded around the exterior thereof, or the Halkey-Roberts type valve 116 may be pressure fit within the retainer 118 an secured in place by an annular projection 120 that engages within a corresponding groove 122 defined by the interior of the retainer 118. A self-sealing silicone valve may also be utilized in place of the Halkey-Roberts type valve 116 to enhance the aesthetic appearance and reduce the size of the exposed portions of the catheter 10, however care must be taken not to puncture or damage the self-sealing valve or the entire catheter 10 is rendered useless.

The inflation lumen 52 can be molded as an integral part of the catheter wall 26 in the proximal portion 16 of the catheter body 12 by inserting a removable wire within the mold along the predetermined path of the inflation lumen, or can be fabricated by placing a corresponding diameter tube within the mold extending between the position of the opening 54 and the injection port 58. The intermediate tube 56 preferably exits the proximal portion 16 of the catheter body 12 at an angle relative to the longitudinal axis 34 and proximal to the seam between the distal portion 14 and proximal portion 16 of the catheter body 12, so as to permit fabrication and cutting of the valve 36 as a separate component, and to prevent the intermediate tube 56 or injection port 58 from interfering with the palpitation of the valve 36 or the discharge of urine from the voiding opening 32. It may further be appreciated that the valve openings 76 are preferably cut through the valve member 38 prior to the distal portion 14 of the catheter body being engagingly mounted and bonded (or otherwise fixedly attached) to the proximal portion 16 of the catheter body 12 to form a complete unitary catheter 10.

Referring particularly to FIGS. 1 and 38–40, it may be appreciated that the collar 20 is molded as a separate unit and mounted on the catheter body 12 prior to insertion of the catheter body 12 within the patient. The collar 20 may be mounted either before or after the distal end 46 of the inflatable balloon 18 has been secured to the catheter body 12, but prior to its inflation. The relative position of the collar 20 along the length of the catheter body 12 is adjusted by rotating the collar 20 relative to the catheter body 12. With helical threads 60 having a constant and uniform pitch, the axial movement of the collar 20 relative to the catheter body 12 will be generally proportional to the relative number of revolutions or the degree of angular rotation between the collar 20 and catheter body 12. Rotation in one direction will move the collar 20 proximally along the catheter body 12, and rotation in the opposite direction will move the collar distally.

Figure 38:
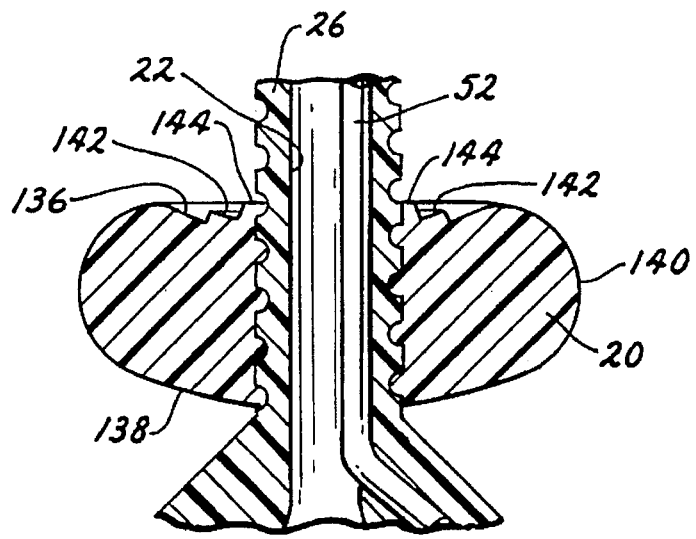
FIG. 38 is a partially broken away side cross section view of an embodiment of the catheter body and collar of this invention showing first and second tiers on the concave top surface of the collar.

FIGS. 1 and 38 show a collar having a generally curved shape with a concave top surface 136, convex bottom surface 138, and a uniformly radiused peripheral surface 140. The peripheral surface 140 may be knurled, patterned, or roughened to provide extra purchase when gripped for adjustment. The concave top surface 136 defines a two-tiered configuration, including a first annular tier 142 sized and designed to exert radial pressure against the labia minora of a female patient, and a second annular tier 144 sized and designed to exert axial pressure surrounding the external orifice of the urethra 126 (or conversely inserted within the orifice of the urethra 126 if desired.)

Figure 39:
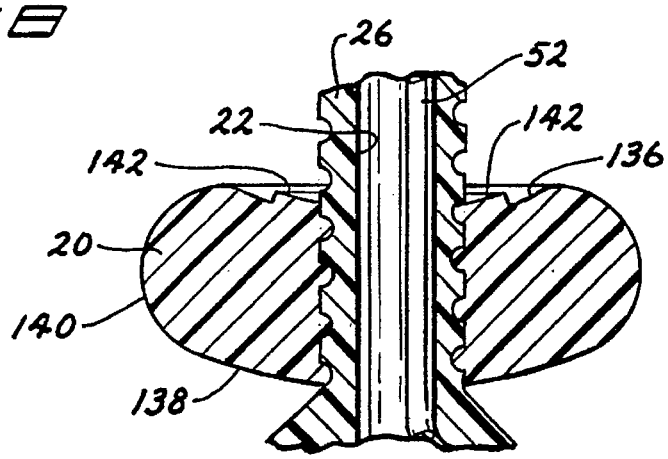
FIG. 39 is a partially broken away side cross section view of an embodiment of the catheter body and collar of this invention showing a single tier on the concave top surface of the collar.
Figure 40:
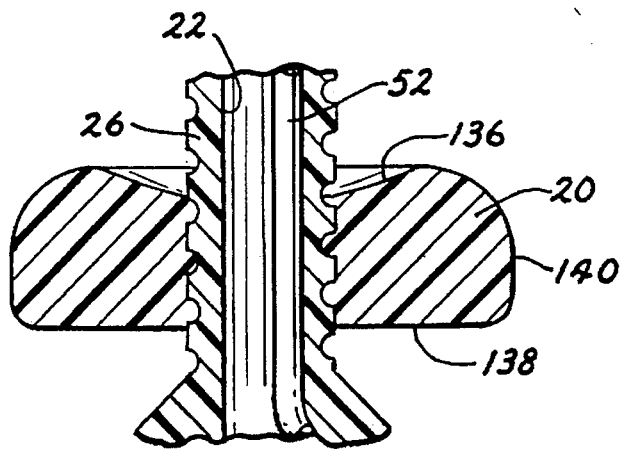
FIG. 40 is a partially broken away side cross section view of an embodiment of the catheter body and collar of this invention showing a concave top surface and a generally planar bottom surface on the collar.

FIG. 39 shows an alternate embodiment of the collar shown in FIG. 38 wherein only the first annular tier 142 is present, and it may be appreciated that a similar embodiment having only the second tier 144 could be fabricated. FIG. 40 shows a third embodiment in which the top surface 136 is concave as with the embodiments shown in FIGS. 1, 38, and 39, but wherein the bottom surface 138 is generally planar and oriented generally perpendicular to the longitudinal axis 34 of the catheter body 26. In such an embodiment, the physician may install the collar 20 onto the catheter body 26 with the concave top surface 136 facing proximally toward the patient, or may invert the collar 20 such that the planar bottom surface 138 faces proximally toward the patient.

While the direction of relative rotation of the collar 20 may be selected as desired, it is deemed advantageous to have a collar 20 move proximally when the catheter body 12 is gripped by the left hand adjacent the valve 36 and the collar 20 is rotated clockwise by the right hand. It may be appreciated that a collar 20 will not be used in all applications, and will generally be utilized only with female patients having shorter urethral lengths and greater need for supplemental anchoring or protection against jarring or displacement of the inflatable balloon 18 and resulting leakage due to contact with the valve 36 or catheter body 12.

The combination of helical threading 60 and mating threading 62 may include helical threading 60 disposed on the catheter body 12 and a non-helical making thread 62 such as an annular projection or ring extending radially inward from the bore of the collar 20, or mating helical threading 60 on bother the catheter body 12 and within the bore of the collar 20.

Referring particularly to FIGS. 14 and 15, the catheter 10 of this invention is shown implanted in a conventional manner within the bladder 124 and urethra 126 of a male and female patient. It may be appreciated that in a male patient, the use of a collar 20 does not provide a suitable option for tensioning the catheter body 26 and inflatable balloon 18. One alternative to the use of a collar 20 is an inflatable member (not shown) disposed adjacent to the exterior of the bladder 124, and another option is to increase the length of the catheter 10 to provide sufficient excess catheter body 26 external to the patient to minimize dislodgement.

Due to the natural permeability of the silicone material from which the inflatable balloon 18 is formed, the fluid (usually physiological saline) used to inflate the inflatable balloon 18 may be treated with an aliquot of a therapeutic agent bactericidal or microbicidal agent that will diffuse through the inflatable balloon 18 into contact with urine within the bladder 124, or alternately will contact urine which diffuses through and into the interior of the inflatable balloon 18. Instead of a bactericidal or microbicidal agent, other therapeutic compounds could be utilized, such as steroids, anti-inflammatory agents, or other medications designed to treat specific conditions.

In addition, because infections tend to migrate or gravitate up the catheter body 12 and urethra 126 toward the bladder 124, the bore and proximal face of the collar 20 and surrounding portion of the catheter body 12 may be coated with an anti-bactericidal or anti-microbicidal agent in a gel or liquid form. Alternately, the material from which the catheter body 12 is fabricated may be impregnated with a predetermined concentration of a bactericidal agent such as silver. The catheter body 12 may also be coated with a friction-reducing agent such as Teflon®, a silicon having a different durometer hardness than the catheter body 12, or various other biocompatible materials selected for their known and intended physiological properties.

In a representative embodiment for female patients as shown in FIGS. 1, 2, and 14, the catheter 10 has an overall length of between 4" and 5" measured between the proximal end 28 and distal end 30, and the inflatable balloon 18 has a relaxed wall thickness of 0.010" compared to a wall thickness for the catheter body of 0.035". The helical threading 60 has alternating lands 134 and grooves 136, with lands 134 of 0.040" width separating ovoid section grooves 136 having a width of 0.040" and a depth of 0.020" or slightly greater. The distal one third of the seating segment 114 is bonded to the catheter body 12, and the entire exposed mating surfaces of the reduced diameter segment 130 and recessed portion 132 are bonded together. It may be readily appreciated that the dimensions of the various components of the catheter 10 will be determined based upon conventional anatomical measurements, and various sizes and shapes for these components will be required to accommodate patients with different anatomical characteristics.

Each element or component of the catheter 10 is fabricated from a synthetic material such as biologically compatible silicone or Kraton®, and assembled with one another using an appropriate biologically compatible adhesive that withstands the temperature and exposure to bodily fluids associated with an indwelling urinary catheter 12 that is used for extended periods of time. Suitable adhesives are known to the art and their selection is a matter of design choice. When silicone is selected as the material for molding the catheter body 12 and inflatable balloon 18, a durometer hardness of about 50 for the balloon inflatable 18, about 70 for the catheter body 12, and about 45–70 for the valve 36 have proven suitable.

Due to the pliability of the materials used to fabricate the catheter 10, a removable reinforcing member (not shown) in the form of a generally straight rod or tube having a radiused tip that is received within the central lumen 22 may be required to provide sufficient stiffness or rigidity to permit insertion of the catheter 10.

A wide variety in the selection of valves 36 and valve member 38 configurations, tolerances, dimensions, hardnesses, materials, and adhesives compared to the representative examples shown and discussed above can be made by those of ordinary skill in the art when fabricating and assembling a urinary catheter 10 according to the teachings set forth herein.

Figure 41:
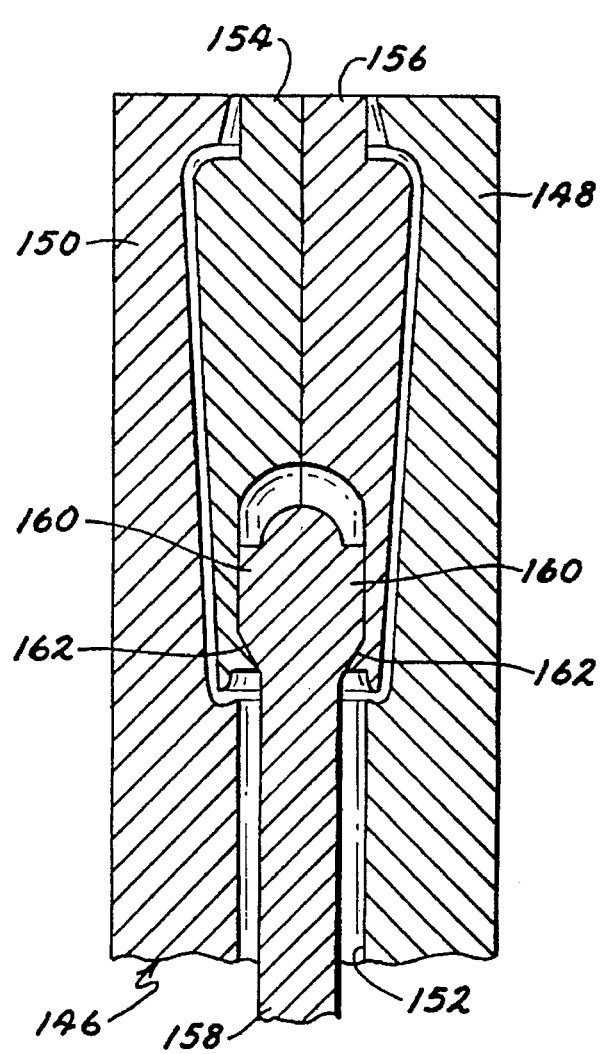
FIG. 41 is a partial cross section view showing the components of the mold and mandril used to fabricate the catheter body, proximal tip, and inflatable balloon of the urinary catheter of FIGS. 2 and 35.
Figure 42:
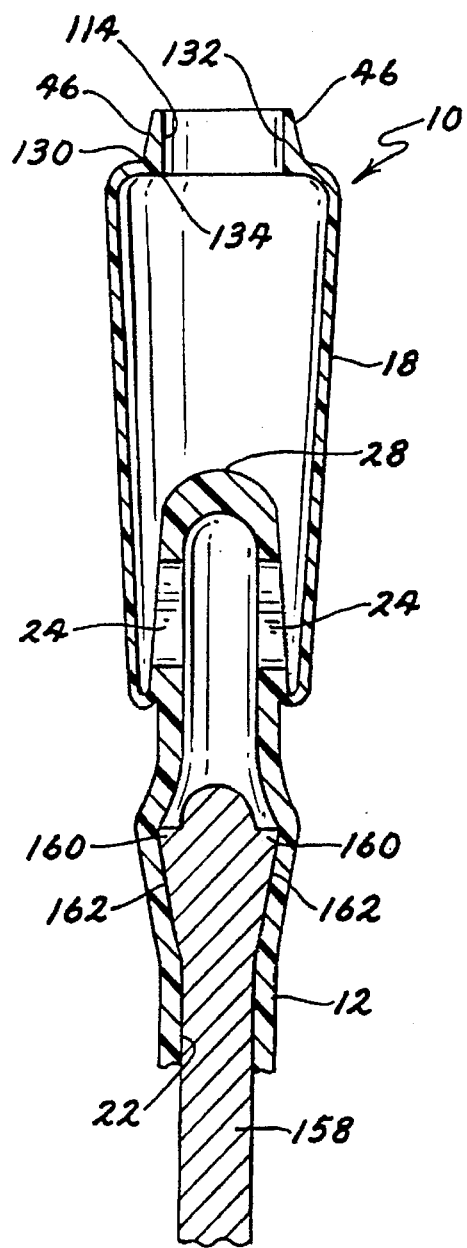
FIG. 42 is a partial cross section view of the proximal end of the urinary catheter molded within the mold of FIG. 41 showing the mandril being removed from the central lumen.

Referring particularly to FIGS. 41 and 42, one embodiment of a mold 146 is disclosed for fabricating the urinary catheter 10 in which the inflatable balloon 18 is connected to and molded unitarily at its proximal end 44 with the proximal portion 16 of the catheter body 12 including the catheter tip 28 and opening 24. The urinary catheter 10 is molded such that it is initially configured with the distal end 46 of the inflatable balloon 18 displaced from the catheter body 12 in an inverted configuration with the inflatable balloon 18 extending in the proximal direction away from the catheter body 12 as previously shown in FIG. 36, with a substantial portion of the balloon 18 being disposed more proximally relative to the tip 28 of the catheter body 12 as shown particularly in FIG. 2. The mold 146 includes a first half 148 and second half 150 which mate to form a hollow interior cavity 152 corresponding to the external shape and configuration of the urinary catheter 10 when molded. A first inner segment 154 and a second inner segment 156 are received within the interior cavity 152 and spaced apart therefrom in a uniform manner to define the wall thickness of the inflatable balloon 18 and the proximal tip 28 of the catheter body 12, with a portion of the interior cavity 152 communicating with the exterior of the mold 146 such that the liquid resin used to form the urinary catheter 10 may be injected within the interior cavity 152. A mandril 158 is similarly inserted within the interior cavity 152 and spaced apart therefrom in a uniform manner to define the wall thickness of the catheter body 12 and the diameter of the central lumen 22. The mandril 158 includes a number of projections 160 equal to the number of openings 24 through the distal tip 28 of the catheter body 12, each projection 160 having an angled or bevelled face 162 mating with a corresponding one of the first inner segment 154 and a second inner segment 156.

Once the urinary catheter 10 has been molded and cured appropriately within the mold 146, the first half 148 and second half 150 of the mold 146 are separated. The first inner segment 154 and a second inner segment 156 may be separated or pivoted apart from one another and withdrawn from the interior of the inverted inflatable balloon 18 with the distal ends riding over the projections 160. The mandril 158 is then withdrawn through the central lumen 22 as shown in FIG. 42, with the projections 160 stretching or deforming the material forming the catheter body 12 as the mandril 158 is withdrawn through the central lumen 22, and returning to the unstretched or relaxed configuration of the urinary catheter 10 once the projections 160 have passed and the mandril 140 withdrawn. Conversely, the mandril 158 could in some instances be withdrawn prior to the first inner segment 154 and a second inner segment 156 being removed from the interior of the inverted inflatable balloon 18, with the first inner segment 154 and a second inner segment 156 of the mold 146 riding over the projections 160 on the mandril 158. It may further be appreciated that the placement and configuration of the projections 160 forming the openings 24 in the proximal tip 28 of the urinary catheter 10 may be adapted or constructed in a variety of ways other than the representative example shown herein.

Referring to FIGS. 43–45, an embodiment of the threaded region of the catheter body 12 and the retention collar 20 are shown in which an antibactericidal or other antiseptic substance 164 such as a betadine-containing gel is initially disposed within the helical threading 60 of the catheter body 12. The mating threading 62 of the retention collar 20 received within the recess formed by the helical threading 60 displaces the antiseptic substance 166 as the retention collar is moved upwardly along the catheter body 12 as shown in FIG. 44, with the antiseptic substance 164 moving to and accumulating on the concave top surface 136 of the retention collar 20. As the top surface 136 of the retention collar 20 is moved into close confronting proximity to or contact with the area of tissue 166 surrounding the distal orifice of the urethra 126 of the patient, the accumulation of antiseptic substance 164 on the concave surface 136 of the retention collar 20 contacts and is compressed against the area of tissue 166. The antiseptic substance 166 thereby fills the voids formed between the concave surface 136 of the retention collar 20 and the area of tissue 166 surrounding the distal orifice of the urethra, thereby forming a barrier preventing or minimizing the migration of infectious contaminants such as bacteria through the orifice of the urethra 126 and proximally along the exterior of the catheter body 12 within the urethra 126, and further forms a liquid seal preventing the egress or leakage of urine from within the urethra 126 through the orifice of the urethra 126 along the exterior of the catheter body 12. Additional quantities of the antiseptic substance 164 may subsequently be added.

Referring again to FIGS. 43–45, the concave surface 136 of the retention collar 20 may optionally define a generally conical projection 168 extending axially from the conical surface 136 proximally toward the urethra 126 and the area of tissue 166 surrounding the orifice of the urethra 126 of the patient. This projection 168 is received within the orifice of the urethra 126 a distance on the order of no more than 5 mm, and preferably on the order of 1–3 mm, when the retention collar 20 is in close confronting contact with the area of tissue 166 surrounding the orifice of the urethra 126, the projection 168 having a diameter such that the outer surface of the projection 168 contacts the interior of the urethra 126 generally proximate to distal orifice thereof to provide an additional sealing contact against leakage or the migration of infection along the exterior of the catheter body 12 within the urethra 126, but does not exert undue pressure radially outward against the urethra 126 so as to create discomfort for the patient or injure the tissue forming the urethra 126.

Figure 46:
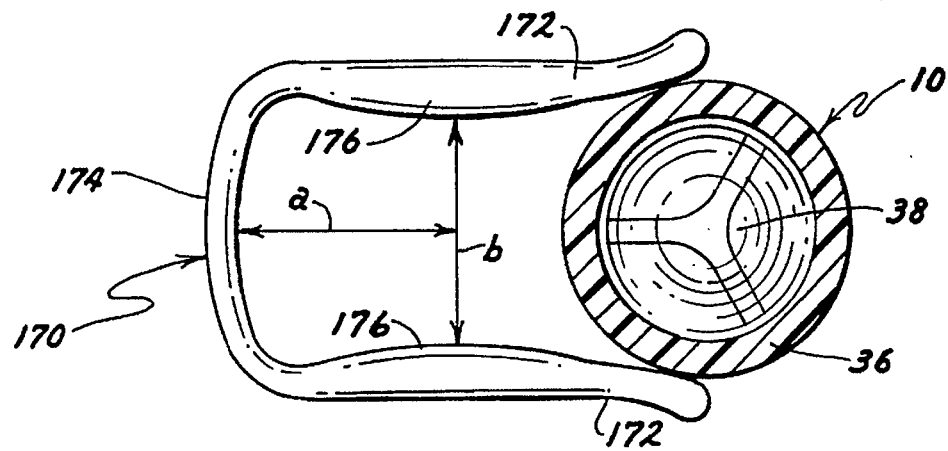
FIG. 46 is a partial cross section view of the valve body showing a clip member in close proximity prior to engagement on the valve body.
Figure 47:
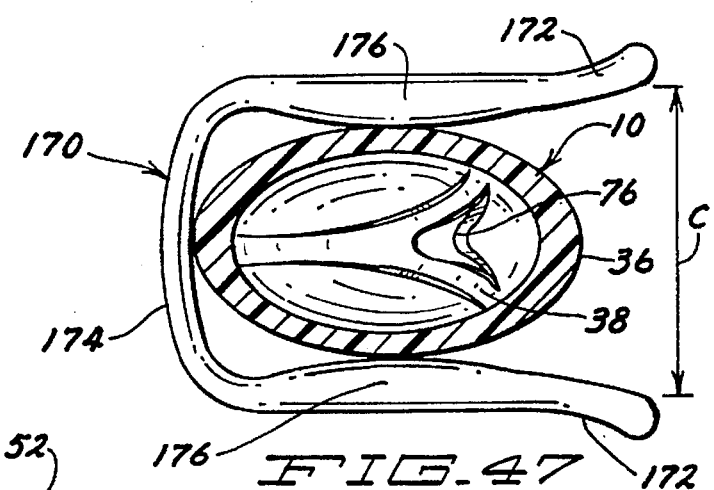
FIG. 47 is a partial cross section view of the valve body showing the clip member engaged on the valve body and deforming the valve member to the open configuration.

Referring to FIGS. 46–47, it may be appreciated that in some instances it may be desirable for a patient to hold the palpitatable valve 36 in the open position with the valve member 38 deformed for extended periods of time to permit drainage, in which case the provision of a releasable clip member 170 to maintain the valve 36 in the open position will be suitable. One embodiment of such a clip member 170 is shown in which a generally U-shaped segment of resilient material such as plastic is provided, the clip member 170 having a pair of generally parallel leg segments 172 joined by a connecting bridge segment 174 having suitable elasticity and plasticity such that the clip member 170 exerts pressure from opposing directions sufficient to deform the valve 36 and maintain the valve 36 in the open position when the clip member 170 is selectively engaged on the valve member 36 as shown in FIG. 47, but permit the valve member 36 to return to the undeformed and closed configuration when the clip member 170 is selectively disengaged from the valve body 36 as shown in FIG. 46. Each leg segment 172 of the clip member 170 may include a generally convex inner surface 176 adapted to apply pressure to the opposing sides of the valve body 36 when the valve body 36 is slidably inserted and received between the leg segments 172, the inner surfaces 176 being spaced apart a distance a equal to the desired deformation of the valve body 36 taking into account the flexure of the leg segments 172 and bridge segment 174 due to the pressure exerted by the deformed valve body 36, the inner surfaces 176 being spaced apart a distance b from the bridge member 174 accounting for the oval or ovoid shape of the deformed valve body 36 such that complete engagement and maximal deformation is achieved when the valve body 36 contacts the bridge segment 174 as shown in FIG. 47. The ends of each leg segment 172 are preferably rounded or radiused, and flare or taper outwardly relative to one another such that a distance e generally equal to or slightly greater than the undeformed diameter of the valve body 36 is provided between the inner surfaces of the leg segments 172 at the ends thereof to permit easy passage of the valve body 36 between the ends of the leg segments 172 as the clip member 170 is being selectively mounted and engaged upon the valve body 36.

Figure 48:
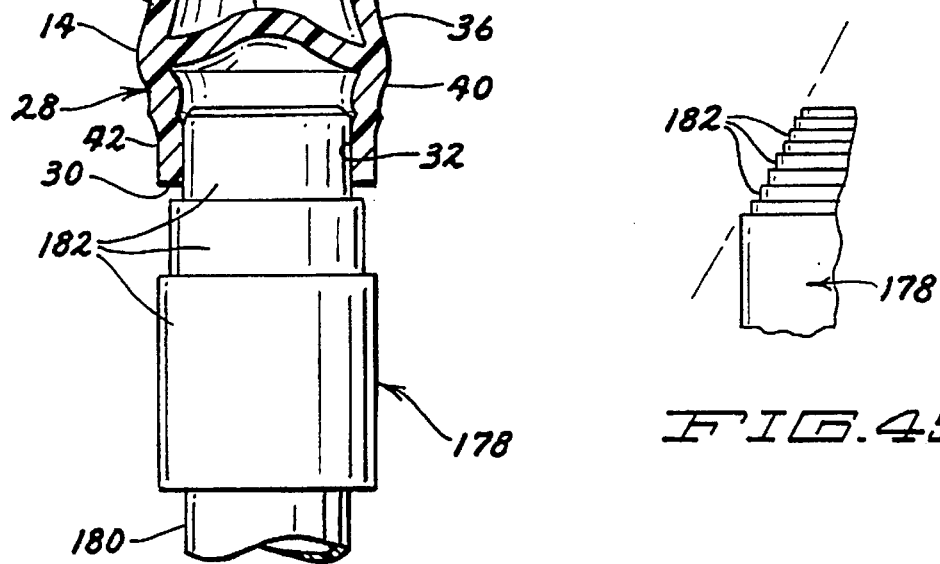
FIG. 48 is a partially broken away cross section view of a prior art Foley-catheter connector and drainage tube partially inserted and engaged within the distal opening of the valve body of FIGS. 1 and 3.
Figure 49:
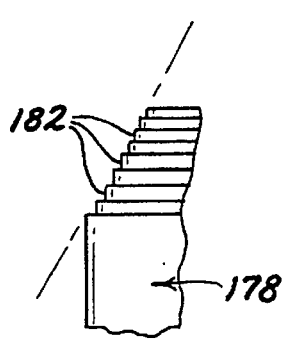
FIG. 49 is a partially broken away cross section view of the tip of a prior art Foley-catheter connector having a multiplicity of steps or tiers approximating a uniform taper.

Referring to FIG. 48, it may be appreciated that the voiding opening 32 at the distal end 30 of the catheter body 12 and the truncated conical segment 42 of the valve wall 40 which define the proximal end 28 of the catheter body 12 are sufficiently pliable and resilient so as to be deformed or stretched to permit the insertion of a conventional Foley-type connector 178 having a drainage tube 180 attached thereto, insertion of such a connector 178 stretching the valve body 36 and deforming the valve member 38 to the open configuration permitting continuous voiding. A connector 178 having a plurality of generally cylindrical outer surfaces 182 of progressively increasing diameter is shown in FIG. 48 as a representative example of such a connector 178, but a connector 178 having a different type of tapered end will will also perform suitably. One alternate connector 178 shown in FIG. 49 includes a multiplicity of generally cylindrical outer surfaces 182 of progressively increasing diameter in which both the change in diameter and the height of each step are generally equal and relatively small, such that in overview the tip of the connector 178 appears to have a generally uniform taper on the order of 30°–60° but is actually composed of a multiplicity of steps or tiers. While it may be appreciated that any sufficiently rigid connector 178 having a diameter greater than the minimum relaxed diameter and less than the maximum stretched diameter of the voiding opening 32 will permit the connector 178 to be inserted into the distal end 30 of the catheter body 12 and engaged therein, the practical use of such an embodiment with connectors 178 already mounted on existing drainage tubes 180 will depend upon the elasticity of the material from which the distal end 30 of the catheter body 12 is fabricated, the frictional coefficient between that material and the connector 178, the diameter of the particular connector 178, and the maximum force normally expected to be exerted on the drainage tube 180. The connector 178 and drainage tube 180 may be quickly disconnected from the distal opening 30 of the catheter 10 by manually applying manual tension or twisting force, and if the connector 178 becomes unintentionally dislodged from the distal end 30 of the catheter body 12 the valve 36 will automatically return to the undeformed and closed configuration.

While the preferred embodiments of the above urinary catheter 10 and method for manufacturing the same as currently contemplated have been described in detail with reference to the attached drawing Figures, it is understood that various changes and adaptations may be made in the urinary catheter 10 without departing from the spirit and scope of the appended claims.

What is claimed is:

1. A urinary catheter for use by a person having a urethra with an orifice, said person further having an area of tissue surrounding said orifice of said urethra, said urinary catheter comprising:

a body member, said body member being at least partially received within the urethra of the person, said body member having an outer surface, said body member defining at least one recessed region extending radially inward from and relative to said outer surface of said body member;

a retaining member, said retaining member being mounted on said body member and movable between a first position and a second position on said body member, at least a portion of said retaining member traversing said at least one recessed region when said retaining member is moved from said first position to said second position, at least a portion of said retaining member being at least partially received within said recessed region when said retaining member is moved from said first position to said second position, said retaining member having a surface closely confronting the area of tissue surrounding the orifice of the urethra when the retaining member is at said second position on said body member; and an antiseptic substance, said antiseptic substance being received within said recessed region of said body member such that said portion of said retaining member received within said recessed region contacts and moves at least a portion of said antiseptic substance from said recessed region to said surface of said retaining member when said retaining member is moved from said first position to said second position, such that said portion of said antiseptic substance moved to said surface accumulates on said surface of said retaining member and contacts the area of tissue surrounding the orifice of the urethra when the retaining member is in the second position.

2. The urinary catheter of claim 1 wherein the body member and retaining member of the urinary catheter and the area of tissue surrounding the orifice of the urethra are exposed to an infectious contaminant, and further wherein the portion of the antiseptic substance that is moved to and accumulates on the surface of the retaining member and contacts the area of tissue surrounding the orifice of the urethra forms a barrier preventing the migration of said infectious contaminant through the orifice and the urethra of the person along the outer surface of the body member of the urinary catheter.

3. The urinary catheter of claim 2 wherein the infectious contaminant is a bacteria and the antiseptic substance is a bactericide.

4. The urinary catheter of claim 1 wherein the urethra of the person contains an aliquot of urine, and further wherein the portion of the antiseptic substance that is moved to and accumulates on the surface of the retaining member and contacts the area of tissue surrounding the orifice of the urethra forms a fluid seal preventing the leakage of said aliquot of urine from within the urethra through the orifice of the urethra along the outer surface of the body portion of the urinary catheter.

5. The urinary catheter of claim 4 wherein the antiseptic substance is a gel.

6. The urinary catheter of claim 4 wherein the antiseptic substance contains a betadine solution.

7. The urinary catheter of claim 1 wherein the surface of the retaining member defines a generally concave region having a shape generally conforming to the area of tissue surrounding the orifice of the urethra, the antiseptic substance accumulating in said concave region.

8. The urinary catheter of claim 1 wherein the portion of the antiseptic substance received within the recessed region of the body member of the urinary catheter is initially generally flush with the outer surface of the body member of the urinary catheter before being moved to the surface of the retaining member.

9. A urinary catheter for use by a person having a urethra with an orifice, said urinary catheter comprising:

a body member, said body member being at least partially received within the urethra of the person; and a retaining member, said retaining member being mounted on said body member and movable between a first position and a second position, said retaining member having a surface closely confronting the orifice of the urethra when said retaining member is moved to said second position, at least a portion of said retaining member being received within the orifice of the urethra when said retaining member is at said second position.

10. The urinary catheter of claim 9 wherein the surface of the retaining member closely confronting the orifice of the urethra defines a generally concave region, the portion of the retaining member received within the orifice of the urethra projecting axially toward the urethra from said generally concave region.

11. The urinary catheter of claim 9 wherein the portion of the retaining member received within the orifice of the urethra has an outer surface defining a generally conical shape.

12. The urinary catheter of claim 9 wherein the portion of the retaining member received within the orifice of the urethra extends less than 5 millimeters into the urethra.

13. The urinary catheter of claim 12 wherein the portion of the retaining member received within the orifice of the urethra extends approximately 1 to 2 millimeters into the urethra.

14. The urinary catheter of claim 12 wherein the portion of the retaining member received within the orifice of the urethra extends approximately 2 to 3 millimeters into the urethra.

15. In a urinary catheter for use by a person having a bladder to control the flow of urine from said bladder, said urinary catheter including a catheter body, a lumen, a palpitatable valve connected to said catheter body in fluid communication with said lumen such that said person selectively manipulates said valve between a closed position and an open position to void said urine from said bladder through said lumen, said palpitatable valve including a valve element defining an opening extending entirely therethrough and disposed in fluid communication with said lumen, said valve element being generally deformable when said person selectively manipulates said valve such that said valve opening permits said flow of urine through said opening, the improvement comprising:

a clip member, said clip member being selectively engaged on the palpitatable valve by the person to deform the valve element and maintain the valve element in a deformed configuration such that the valve permits the flow of urine through the opening of the valve element, the valve element returning to an undeformed configuration when said clip member is selectively disengaged from the palpitatable valve by the person such that the valve prevents the flow of urine through the opening of the valve element.

* * * * *

UNITED STATES PATENT AND TRADEMARK OFFICE
CERTIFICATE OF CORRECTION

PATENT NO. : 5,624,395
DATED : April 29, 1998
INVENTOR(S) : Mikhail, et. al.

It is certified that error appears in the above-indentified patent and that said Letters Patent is hereby corrected as shown below:

Column 15, Line 4, please delete "3A" and insert --3/4--;

Column 17, Line 45, please delete "sorer" and insert --softer--;

Column 24, Line 43, after "distance" please delete "a" and insert in bold text --a--;

Column 24, Line 48 after "distance" please delete "b" and insert in bold text --b--; and Column 24, Line 54 after distance" please delete "e" and insert in bold text --c--.

Signed and Sealed this

Thirtieth Day of June, 1998

*Attest:*

BRUCE LEHMAN

*Attesting Officer*     *Commissioner of Patents and Trademarks*